US012766044B2

(12) United States Patent
Langdon et al.

(10) Patent No.: US 12,766,044 B2
(45) Date of Patent: Oct. 20, 2026

(54) BODY-CONFORMABLE ABSORBENT ARTICLE

(71) Applicant: The Procter & Gamble Company, Cincinnati, OH (US)

(72) Inventors: Frederick Michael Langdon, Cincinnati, OH (US); Timothy Ian Mullane, Union, KY (US); Bret Darren Seitz, Loveland, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 323 days.

(21) Appl. No.: 18/508,290

(22) Filed: Nov. 14, 2023

(65) Prior Publication Data

US 2024/0156647 A1 May 16, 2024

Related U.S. Application Data

(60) Provisional application No. 63/424,979, filed on Nov. 14, 2022.

(51) Int. Cl.
*A61F 13/15* (2006.01)
*A61F 13/53* (2006.01)

(52) U.S. Cl.
CPC .. *A61F 13/15203* (2013.01); *A61F 13/15707* (2013.01); *A61F 13/53* (2013.01); *A61F 2013/530802* (2013.01)

(58) Field of Classification Search
CPC ........ A61F 13/534; A61F 2013/530817; A61F 13/53; A61F 13/532; A61F 13/15707;
(Continued)

(56) References Cited

U.S. PATENT DOCUMENTS 5,260,345 A * 11/1993 Des ........................ A61F 13/532 521/905
5,518,801 A * 5/1996 Chappell ........... A61F 13/51484 428/167
(Continued)

FOREIGN PATENT DOCUMENTS

EP 0804917 A1 * 11/1997 ........ A61F 13/47263
EP 0815817 A1 * 1/1998 ........ A61F 13/47227
(Continued)

OTHER PUBLICATIONS

PCT Search Report and Written Opinion for PCT/US2023/079556 dated Mar. 11, 2024, 11 pages.

*Primary Examiner* — Adam Marcetich
(74) *Attorney, Agent, or Firm* — Amanda Herman Berghauer

(57) ABSTRACT

An absorbent article having a liquid permeable topsheet, a liquid impermeable backsheet, and an absorbent structure comprising an open-celled absorbent foam material disposed between the topsheet and backsheet. The absorbent article has been incrementally stretched along at least a first and second stretch direction, such that the topsheet and backsheet each comprise plastically stretched zones disposed substantially along a first plurality of lines of deformation being substantially perpendicular to the first stretch direction and a second plurality of lines of deformation being substantially perpendicular to the second stretch direction. The absorbent foam material is fractured substantially along the first and second plurality of lines of deformation into a plurality of discrete foam pieces that are separated from neighboring pieces by a gap. An adhesive is positioned between the topsheet and the discrete foam pieces and bonds the discrete foam pieces to the topsheet.

16 Claims, 22 Drawing Sheets

(58) Field of Classification Search
CPC ........ A61F 13/535; A61F 2013/530802; A61F 13/51104; A61F 13/47; A61F 13/53708; A61F 13/15; A61F 13/15634; A61F 13/531; A61F 2013/530649; A61F 13/15731; A61F 13/511; B29C 55/18; B32B 5/18; B32B 27/065; B29K 2105/04; B29K 2105/045
See application file for complete search history.

(56) References Cited

U.S. PATENT DOCUMENTS

| | | | | |
|---|---|---|---|---|
| 5,756,039 | A | 5/1998 | Mcfall | |
| 5,941,863 | A * | 8/1999 | Guidotti ................ | A61F 13/535 604/374 |
| 5,993,431 | A | 11/1999 | Mcfall | |
| 6,203,654 | B1 | 3/2001 | Mcfall et al. | |
| 6,316,688 | B1 | 11/2001 | Hammons | |
| 6,383,431 | B1 | 5/2002 | Dobrin | |
| 6,410,820 | B1 | 6/2002 | Mcfall et al. | |
| 7,056,404 | B2 | 6/2006 | Mcfall et al. | |
| 2015/0335498 | A1* | 11/2015 | Hubbard, Jr. ......... | A61F 13/536 604/378 |
| 2018/0296403 | A1* | 10/2018 | Kobayashi ........ | A61F 13/15723 |
| 2021/0038444 | A1* | 2/2021 | Rawat ................. | A61F 13/5116 |
| 2021/0290449 | A1* | 9/2021 | Smet ................. | A61F 13/15804 |
| 2022/0226169 | A1* | 7/2022 | Nakaoka ............... | A61F 13/539 |

FOREIGN PATENT DOCUMENTS

| | | | | |
|---|---|---|---|---|
| JP | 2021041145 | A | 3/2021 | |
| WO | 1992015444 | A1 | 9/1992 | |
| WO | WO-2022220758 | A1 * | 10/2022 | ....... A61F 13/15707 |

* cited by examiner

BODY-CONFORMABLE ABSORBENT ARTICLE

CROSS REFERENCE TO RELATED APPLICATIONS

This application claims the benefit, under 35 U.S.C. § 119(e), to U.S. Provisional Application No. 63/424,979, filed Nov. 14, 2022, the entire disclosure of which is fully incorporated by reference herein.

FIELD OF THE INVENTION

The present disclosure relates to a body-conformable absorbent article and method of manufacturing such absorbent articles.

BACKGROUND OF THE INVENTION

Women have been using absorbent articles such as feminine hygiene pads, also known as sanitary napkins, for many years to intercept, contain, absorb and retain discharged menstrual fluid, and avoid soiling of underwear, outer garments, bedding, etc., during menses.

In order to serve its intended function well, ideally, a feminine hygiene pad should:

- closely conform to the wearer's body to intercept discharged fluid moving along skin surfaces and prevent it from escaping the pad;
- readily accept and draw in discharged fluid;
- readily absorb the fluid;
- have absorption capacity for a duration of wear and associated discharge volume sufficient for reasonable wearer/user convenience;
- resist allowing absorbed fluid to be wicked from absorbent materials back to the wearer-facing surfaces (which can result in an undesirable wet feel against the wearer's skin);
- resist allowing absorbed fluid to be expressed from the pad, under pressure imposed on the pad from, e.g., shifting body movements, sitting, etc.; and
- reliably remain suitably positioned within the wearer's underwear during the duration of wear, while accommodating stretch and movement of the underwear fabric with the wearer's body movements.

Additionally, many users prefer in some circumstances that the pad be relatively small and/or thin (relatively low surface area and/or low bulk/caliper) so as to be discreet when worn under snug-fitting and/or revealing outer clothing. Users also typically prefer that the pad be comfortable to wear, i.e., soft-feeling, compliant and/or "breathable," i.e., vapor permeable (to allow water vapor to escape and prevent the pad from feeling uncomfortably warm and/or prevent overhydration of the wearer's skin areas beneath the pad while worn).

It will be appreciated that it is difficult to design a feminine hygiene pad having a combination of component materials and configuration that perfectly meets all of these objectives, because they are, to some extent, conflicting. For example, sufficient absorption capacity generally requires a minimum volume and/or quantity of absorbent materials, which may come at the expense of small size, low bulk/caliper and flexibility or conformability. As another example, absorbent materials currently used in many feminine hygiene pads, including combinations including cellulose fiber, are effective for purposes of fluid wicking and absorbency, but do not contribute to (and in many cases hinder) configuration of a pad that is particularly flexible, compliant or body-conformable.

Accordingly, there remains room for improvement in combinations of component materials and configurations of feminine hygiene pads, that more effectively meet more of the objectives identified above.

SUMMARY OF THE INVENTION

Described herein is an absorbent article comprising a longitudinal axis and a lateral axis; a liquid permeable topsheet having a garment-facing surface and an opposing wearer-facing surface; a liquid impermeable backsheet having a garment-facing surface and an opposing wearer-facing surface; and an absorbent structure comprising an open-celled absorbent foam material disposed between the topsheet and the backsheet. The absorbent article has been incrementally stretched along at least a first stretch direction and a second stretch direction differing from the first stretch direction, such that: the topsheet and the backsheet each comprise plastically stretched zones disposed substantially along a first plurality of lines of deformation being substantially perpendicular to the first stretch direction and a second plurality of lines of deformation being substantially perpendicular to the second stretch direction. The absorbent foam material is fractured substantially along the first plurality of lines of deformation and the second plurality of lines of deformation into a plurality of discrete foam pieces, wherein the discrete foam pieces are separated from neighboring pieces by a gap. From about 15 gsm to about 35 gsm of an adhesive is positioned between the garment-facing surface of the topsheet and a wearer-facing surface of the discrete foam pieces and bonds the discrete foam pieces to the topsheet.

Also described herein is an absorbent article comprising a longitudinal axis and a lateral axis; a liquid permeable topsheet having a garment-facing surface and an opposing wearer-facing surface; a liquid impermeable backsheet having a garment-facing surface and an opposing wearer-facing surface; and an absorbent structure comprising an open-celled absorbent foam material disposed between the topsheet and the backsheet. The topsheet and the backsheet each comprise plastically stretched zones disposed substantially along a first plurality of lines of deformation extending in a first direction and a second plurality of lines of deformation extending in a second direction. The first plurality of lines of deformation form an angle $\alpha$ with respect to the longitudinal axis and the second plurality of lines of deformation form an angle $\beta$ with respect to the longitudinal axis, wherein the angle $\alpha$ and the angle $\beta$ are each from about 5 degrees to 85 degrees. The absorbent structure comprises a plurality of discrete foam pieces arranged along the lines of deformation, wherein the discrete foam pieces are separated from neighboring pieces by a gap of from 0.3 mm to 1.2 mm.

Also described herein is an absorbent article comprising a longitudinal axis and a lateral axis; a liquid permeable topsheet; a liquid impermeable backsheet having a basis weight of from about 20 gsm to about 28 gsm; and an absorbent structure comprising a high internal phase emulsion foam disposed between the topsheet and the backsheet. The topsheet and the backsheet each comprise plastically stretched zones, wherein a portion of the plastically stretched zones extend continuously from a first side of the topsheet to a second side of the topsheet. The absorbent structure comprises a plurality of discrete foam pieces arranged in a pattern extending across the entire absorbent structure, wherein the discrete foam pieces are separated from neighboring pieces by a gap of greater than 0.1 mm.

DETAILED DESCRIPTION OF THE INVENTION

Definitions

Figure 1:
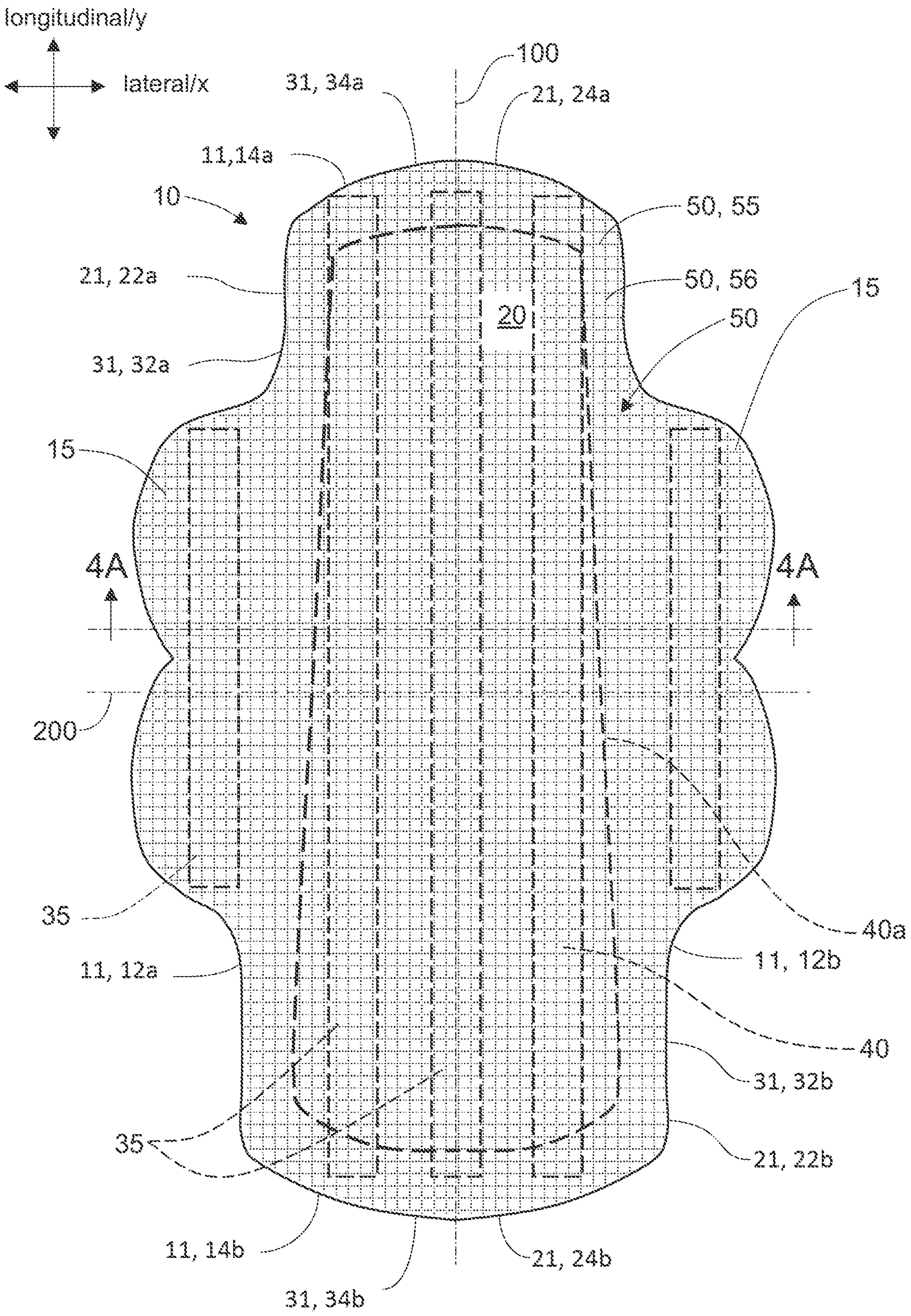
FIG. 1 is a plan view of an example of an absorbent article in the form of a feminine hygiene pad, wearer-facing side up, illustrating one example of a pattern of bidirectional deformation.

For purposes herein, the following terms will have the meanings set forth:

"Absorbent article" means a layered product including an absorbent structure and configured to be worn externally about the lower torso and/or crotch region of a human being, and configured to contain and/or absorb bodily exudates which may include urine, menstrual fluid or feces. Examples of absorbent articles include feminine hygiene pads (also known as catamenial pads or sanitary napkins), panty liners, menstrual underwear, incontinence pads, absorbent underwear (configured for, e.g., managing incontinence), diapers and training pants.

"Bidirectional"—with respect to a layered composite web structure or any layer component thereof, refers to the directions of two axes in an x-y plane, which intersect at a smaller angle ranging from 20 degrees to 90 degrees.

A web, sheet or film material, or a laminate or composite thereof, is considered to be "extensible" for purposes herein if, when a tensile force no greater than 50 gf/mm (gf per mm of sample width, where width is measured perpendicular to the stretch direction) is applied to the subject material along a stretch direction, the material may be extended along the direction to an elongated dimension of at least 110% of its original relaxed dimension (i.e., it can extend by at least 10% of its original relaxed dimension), without substantial fracture or breakage which substantially damages the subject web, sheet or film material, or laminate or composite thereof. For purposes herein plastic deformation is not considered substantial damage.

For purposes herein, a web, sheet or film material, or a laminate or composite thereof is “elastic” or “elastically extensible” for purposes herein if, when a tensile force no greater than 50 gf/mm (gf per mm of sample width, where width is measured perpendicular to the stretch direction) is applied to the subject material along a stretch direction, the material may be extended along the direction to an elongated dimension of at least 110% of its original relaxed dimension (i.e., it can extend by at least 10% of its original relaxed dimension), without rupture or breakage which substantially damages the subject web, sheet or film material, or laminate or composite thereof; and when the force is removed from the subject material, the material retracts along the stretch direction to recover at least 40% of such elongation. To illustrate, if a section of fabric having an original relaxed length of 100 mm and a width of 40 mm can be elongated by tensile force of 2000 gf (50 gf/mm) in a direction along its length to 110 mm length without substantial damage, and will retract upon removal of the force to a length no greater than 106 mm (110 mm−106 mm=4 mm=40% of 10 mm), it is “elastic” as defined herein. “Elongation,” used herein to quantify and express an amount of strain imparted to an elastic material in a stretch direction, means: {[(strained length of the strand)−(length of the strand before straining)]/(length of the strand before straining)}, ×100%.

“Joined” encompasses configurations whereby an element is directly secured to another element by affixing the element directly to the other element, and configurations whereby an element is indirectly secured to another element by affixing the element to intermediate member(s), which, in turn are affixed to the other element.

“Lateral”—with respect to an absorbent article or a component thereof, refers to a direction parallel to a horizontal line tangent to the front surfaces of the upper portions of wearer’s legs proximate the torso, when the article is being worn normally and the wearer has assumed an even, square, normal standing position. A “width” dimension of any component or feature of an absorbent article is measured along the lateral direction. When the absorbent article or component thereof is laid out flat on a horizontal surface, the “lateral” direction corresponds with the lateral direction relative the structure when it is worn, as defined above. With respect to an absorbent article that is opened and laid out flat on a horizontal planar surface, “lateral” refers to a direction perpendicular to the longitudinal direction and parallel to the horizontal planar surface.

The “lateral axis” of an absorbent article or component thereof is a lateral line lying in an x-y plane and equally dividing the length of the article or the component when it is opened and laid out flat on a horizontal surface. A lateral axis is perpendicular to a longitudinal axis.

“Longitudinal”—with respect to an absorbent article or a component thereof, refers to a direction perpendicular to the lateral direction. A “length” dimension of any component or feature of a layered absorbent structure is measured along the longitudinal direction from its forward extent to its rearward extent. When the absorbent article or component thereof is laid out flat on a horizontal surface, the “longitudinal” direction is perpendicular to the lateral direction relative the structure when it is worn, as defined above.

The “longitudinal axis” of an absorbent article or component thereof is a longitudinal line lying in an x-y plane and equally dividing the width of the article, when the article is opened and laid out flat on a horizontal surface. A longitudinal axis is perpendicular to a lateral axis.

“Liquid impermeable”—refers to one or more properties or features of a film, web material or laminate thereof that cause(s) it to resist passage of aqueous liquid therethrough (from one major surface through to the other opposite major surface), under ordinary conditions of use of absorbent articles. A film, web material or laminate thereof may be liquid impermeable, but also vapor permeable (“breathable”).

“Machine direction”—with respect to a process for manufacturing a web material or a laminate or layered arrangement of web materials, refers to the primary direction of conveyance of the materials along the manufacturing line, viewed from above the manufacturing line. It will be understood that the machine direction may change in absolute directional orientation in space at particular locations along the line, if the manufacturing line is so configured. With respect to an individual roller or nip between a pair of rollers, over or in which a web material or combination of web materials is conveyed, laminated or deformed on a manufacturing line, the “machine direction” is ordinarily perpendicular to the axis(es) of the roller(s), and the “cross direction” is ordinarily parallel to the axis(es) of the rollers.

“Permanently mechanically deformed”—means plastically deformed, fractured or broken, or having individual fiber constituents that have been plastically deformed, fractured, broken and/or directionally realigned or reoriented, by application of mechanical force.

“x-y plane,” with reference to an absorbent article or component thereof when laid out flat on a horizontal surface, means any horizontal plane occupied by the horizontal surface or any layer of the article or component.

“z-direction,” with reference to an absorbent article or component thereof when laid out flat on a horizontal surface, is a direction orthogonal to the x-y plane. When the article is being worn by a user (and thus has been urged into a curving configuration), the “z-direction” at any particular point location on the pad refers to a direction normal to the wearer-facing surface of the pad at the particular point location.

With respect to an absorbent article or component thereof, the terms “front,” “rear,” “forward” and “rearward” and similar relative locational terms relate to features or regions of the pad corresponding to the position they would occupy as ordinarily worn by a user, corresponding with the front (anterior) and rear (posterior) of the wearer/user’s body when standing.

With respect to an absorbent article, “wearer-facing” is a relative locational term referring to a feature of a component or structure of the article that when in use that lies closer to the wearer than another feature of the component or structure that lies along the same z-direction line. For example, a topsheet has a wearer-facing surface that lies closer to the wearer than the opposite, outward-facing surface of the topsheet.

With respect to an absorbent article, “outward-facing” (sometimes referred to herein as “garment-facing”) is a relative locational term referring to a feature of a component or structure of the article that when in use that lies farther from the wearer than another feature of the component or structure that lies along the same z-direction line. For example, a topsheet has an outward-facing surface that lies farther from the wearer than the opposite, wearer-facing surface of the topsheet.

The terms “top,” “bottom,” “upper,” “lower,” “over,” “under,” “beneath,” “superadjacent,” “subjacent,” and similar vertical positional terms, when used herein to refer to layers, components or other features of a wearable absorbent article, are to be interpreted with respect to the article as it would appear when opened and laid out flat on a horizontal surface, with its wearer-facing surface facing upward and outward-facing surface facing downward.

Description

The present disclosure relates to absorbent articles, and more particularly, to absorbent articles having improved flexibility and conformability. In some configurations, the absorbent article may comprise a liquid permeable topsheet, a liquid impermeable backsheet, and an absorbent structure disposed between the topsheet and the backsheet. The absorbent structure together with one or both of the topsheet and backsheet may be incrementally stretched, causing permanent deformation of the topsheet and/or backsheet and fracture of the absorbent structure into discrete pieces. It was surprisingly found that an absorbent article with non-orthogonal bidirectional deformation more readily shifts and accommodates a wearer's body movements (e.g., walking) when adhered to the inside of the wearer's underwear. The absorbent article described herein can bend, flex, and stretch with the wearer's underwear, allowing the article to stay in close contact with the body as she moves and creating a more comfortable experience for the wearer, while still keeping the discrete pieces of absorbent structure in place.

Figure 4A:
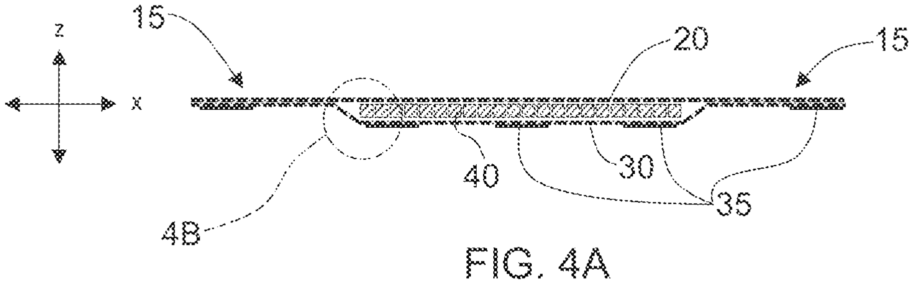
FIG. 4A is a schematic lateral cross section of the article shown in FIG. 1, taken through line 4A-4A in FIG. 1.
Figure 4B:
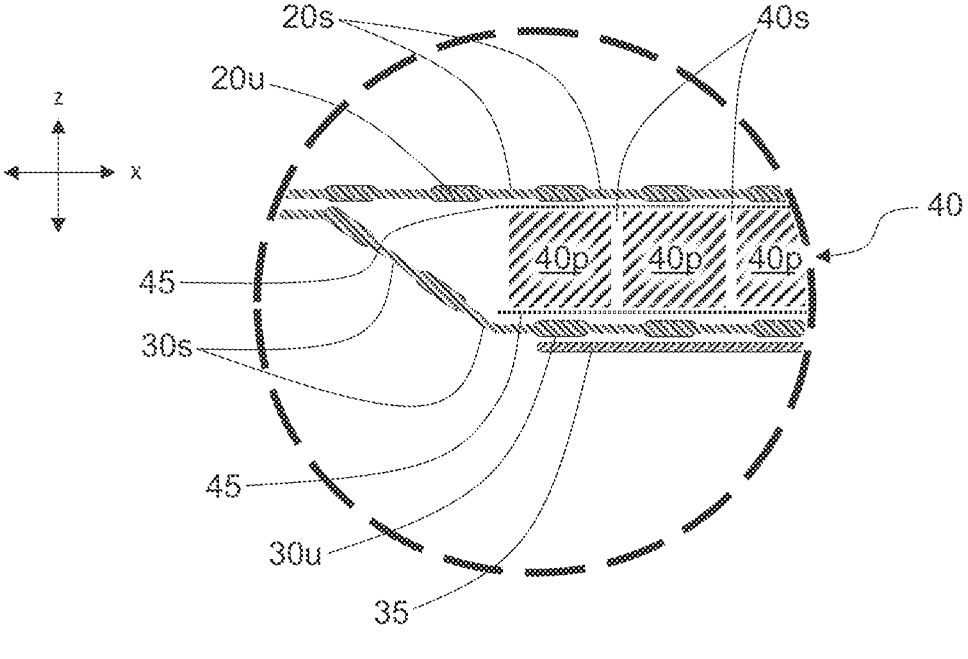
FIG. 4B is an enlarged view of the portion of FIG. 4A shown encircled in circle 4B, in FIG. 4A, in one possible example.

Referring to FIGS. 1 and 4A, an absorbent article 10 (shown here in the form of a feminine hygiene pad) may include a liquid permeable topsheet 20, a liquid impermeable backsheet 30 and an absorbent structure 40 disposed between the topsheet and the backsheet. The absorbent structure has an outer perimeter 40*a*. In regions outside the outer perimeter 40*a*, the topsheet and the backsheet may be bonded together in laminate configuration by any suitable mechanism including but not limited to adhesive bonding, thermal bonding, pressure bonding, etc., thereby retaining and holding the absorbent structure 40 in an enveloped space between the topsheet 20 and the backsheet 30. Article 10 may include opposing wing portions 15 extending laterally outside of perimeter 40*a* by a comparatively greater width dimension than that of the forwardmost and rearwardmost portions of the pad. The outer surface of the backsheet forming the undersides of the main portion and the wing portions 15 may have deposits of adhesive 35 thereon. Adhesive deposits 35 may be provided to enable the user to adhere the pad to the inside of her underpants in the crotch region thereof, and to wrap the wing portions 15 through and around the inside edges of the leg openings of the underpants and adhere them to the outside/underside of the underpants in the crotch region, providing supplemental holding support and helping to protect the insides of the leg edges of the underpants against soiling. When article 10 is packaged, adhesive deposits 35 may be covered by one or more sheets of release film or paper (not shown) that covers/shields the adhesive deposits 35 from contact with other surfaces until the user is ready to remove the release film or paper and place the pad in her underpants for wear/use.

Topsheet

Topsheet 20 may be formed of any suitable nonwoven web material that has plastic/non-elastic extensibility suitable for the purposes described herein. Referring back to the figures, the topsheet 20 is positioned adjacent a wearer-facing surface of the absorbent structure 40 and may be joined thereto and to the backsheet 30 by any suitable attachment or bonding method. The topsheet 20 and the backsheet 30 may be joined directly to each other in the peripheral regions outside the perimeter 40*a* of the absorbent structure 40 and may be indirectly joined by directly joining them respectively to wearer-facing and outward-facing surfaces of the absorbent structure.

The article 10 may have any known or otherwise effective topsheet 20, such as one which is compliant, soft feeling, and non-irritating to a wearer's skin. A suitable topsheet material will include a liquid pervious material that is comfortable when in contact with the wearer's skin and permits discharged menstrual fluid to rapidly penetrate through it. A suitable topsheet may be made of any of various materials such as woven or knitted materials, nonwoven web materials, or apertured films.

Nonlimiting examples of nonwoven web materials that may be suitable for use to form the topsheet 20 include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452. Particularly suitable topsheet materials may include a spunbond nonwoven material comprising polyethylene (PE)/polypropylene (PP) bicomponent fibers (PE sheath and PP core).

In some configurations, the topsheet may be a highly extensible nonwoven web comprising staple or continuous multi-component fibers, such as, for example, described in US 2020/0337910A1. A highly extensible nonwoven web may be beneficial to reduce fiber breakage under mechanical processing that may cause a nonwoven web to experience high strain forces, for example during the incremental stretching process. In the absorbent article context, this may have the desirable effect of reducing the amount of broken fibers that stick to the skin of a wearer. In some configurations, the topsheet may comprise a first polymer component having a first melting temperature and a second polymer component having a second melting temperature. The first polymer component may have a low crystallinity of between about 10% and about 41%, between about 15% and about 38%, between about 20% and about 35%, between about 25% and about 33%, or between about 28% and about 30%, for example, specifically reciting all 0.1% increments within the specified ranges and all ranges formed therein or thereby. Crystallinity may be measured in the fibers or nonwoven web comprising the fibers according to the Crystallinity Test disclosed herein. The first polymer component may have a melting temperature of between about 130° C. and about 161° C., between about 130° C. and about 155° C., or between about 135° C. and about 155° C., for example, specifically reciting all 0.1° C. increments within the specified ranges and all ranges formed therein or thereby. Without wishing to be bound by theory, it is believed that a polymer with low crystallinity may increase the extensibility of a fiber by increasing the ultimate tensile strength of the fiber. In one example, polypropylene with a crystallinity of between about 20% and about 41% may be the first polymer of a multi-component fiber nonwoven web. In another example, polyethylene terephthalate with a crystallinity of between about 20% and about 41% may be the first polymer of a multi-component fiber nonwoven web. A second polymer component may have a high crystallinity of between about 40% and about 80%, between about 45% and about 75%, between about 50% and about 70%, or between about 55% and about 65%, for example, specifically reciting all 0.1% increments within the specified ranges and all ranges formed therein or thereby. Without wishing to be bound by theory, it is believed that a polymer with high crystallinity may increase the tensile strength of a fiber and the tensile strength of a nonwoven web comprising such a fiber. The second polymer component may optionally have a melting temperature that is the same as or lower than that of the first polymer component. In one example, polyethylene may be the second polymer component of a multi-component continuous fiber.

In the context of a nonwoven web comprising continuous bi-component fibers, a first polymer component may be or may comprise polypropylene having a crystallinity of between about 20% and about 41%. The polypropylene may have a melting temperature of between about 130° C. and 161° C. The second polymer component may be or may comprise polyethylene having a crystallinity of between about 45% and about 75%. The polyethylene may have a speed of crystallization of between about 1300 ms and about 1360 ms. The polyethylene may have a melting temperature of between about 100° C. and about 140° C. The bi-component fibers may have a core/sheath configuration, wherein the polypropylene forms the core of the fiber, and wherein the polyethylene forms the sheath of the fiber, partially or completely surrounding the polypropylene core. Without wishing to be bound by theory, it is believed that the low-crystallinity polypropylene fiber core may be used to produce a nonwoven web with improved tensile properties, including increased extensibility. Additionally, it is believed that a sheath material with high crystallinity and a fast crystallization time partially or completely surrounding the core material during fiber spinning may protect the core material and achieve a more amorphous structure in the finished fiber.

In another example, a first polymer component of a bi-component continuous fiber may be polyethylene terephthalate (PET) having a crystallinity of between about 20% and about 41%. The second polymer component may be polyethylene. The continuous fibers may comprise a core/sheath structure where the PET may form the core of the fiber and the polyethylene may partially or completely surround the PET and form the sheath of the fiber.

In some configurations, the topsheet may comprise a highly extensible nonwoven web having an extensibility of between about 300% and about 500%, between about 305% and about 450%, between about 310% and about 425%, between about 315% and about 400%, or between about 320% and about 375%, specifically reciting all 1% increments within the specified ranges and all ranges formed therein or thereby, according to the High Speed Tensile Test. A highly extensible nonwoven web with an extensibility within the ranges stated above may be beneficial to reduce fiber breakage under mechanical processing that may cause a nonwoven web to experience high strain forces. Reduced fiber breakage may result in a stronger nonwoven web with reduced lint.

In some configurations, the topsheet 20 may comprise a plurality of apertures. In some configurations, it may be preferable to have a topsheet that does not comprise apertures to help keep the foam pieces from escaping the article during use.

In some configurations, the topsheet 20 may have a basis weight of about 10 gsm (herein, "gsm" means grams/$m^2$) to about 50 gsm, of from about 22 gsm to about 45 gsm, or from about 25 gsm to about 30 gsm, specifically reciting all values within these ranges and any ranges created thereby.

In some configurations, the topsheet 20 may comprise tufts as described in U.S. Pat. Nos. 8,728,049; 7,553,532; 7,172,801; 8,440,286; 7,648,752; and 7,410,683. The topsheet 20 may have a pattern of discrete hair-like fibrils as described in U.S. Pat. No. 7,655,176 or 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651.

As contemplated herein, component nonwoven web material from which topsheet 20 may be cut may be a nonwoven web material that includes or even consists predominantly (by weight) or entirely of cellulosic plant fibers such as fibers of cotton, flax, hemp, jute or mixtures thereof, that are either naturally hydrophilic or suitably processed so as be rendered hydrophilic (or have increased hydrophilicity), and processed to be suitably soft-feeling against the skin. In some circumstances plant-based fibers may be preferred to appeal to consumer preferences for natural products. In other examples, semisynthetic fibers derived from cellulosic material, such as rayon (for purposes herein, "rayon" includes viscose, lyocell, MODAL (a product of Lenzing AG, Lenzing, Austria) and cuprammonium rayon) may be included as a component of the nonwoven.

The nonwoven web may be formed via any suitable process by which fibers of finite lengths (e.g. staple fibers) may be distributed and accumulated in a controlled fashion onto a forming belt to form a batt having a desired distribution of fibers, to a desired basis weight. Suitable processes may include carding, airlaying and wetlaying. The batt may be processed to consolidate the fibers and entangle them in the z-direction, by processes that may include calendering, needlepunching and hydroentanglement via water jets.

In some examples a topsheet cut from a nonwoven including or consisting predominately (by weight) or entirely of plant fibers, such as cotton fibers, may be preferred. In some examples, the nonwoven web material may be formed via a carding process. In other examples, the nonwoven web material may be formed via an airlaying or wetlaying process. In some examples the nonwoven web material may be a spunbond web including single-component continuous fibers spun from polymeric resin, or alternatively, bi-component or multi-component fibers, or a blend of single-component fibers spun of differing polymer resins, or any combination thereof. In some examples a web may be formed in a co-forming process in which plant-based fibers of finite lengths are physically blended or mixed with streams of spun fibers of longer but indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

In order to ensure that fluid contacting the top (wearer-facing) surface of a hydrophilic topsheet will move suitably rapidly via capillary action in a z-direction to the bottom (outward-facing) surface of the topsheet where it can be drawn into the absorbent structure, it may be important to ensure that the nonwoven web material forming the topsheet has an appropriate weight/volume density, reflecting suitable presence of interstitial passageways among and between the constituent fibers, through which fluid may move within the nonwoven material. A nonwoven with fibers that are consolidated too densely may have insufficient numbers and/or volume of interstitial passageways, and the nonwoven may obstruct rather than facilitate rapid z-direction fluid movement. On the other hand, a nonwoven with fibers that are not consolidated enough to provide sufficient fiber-to-fiber contact and/or sufficiently small interstitial passageways may provide insufficient potential for wicking in the z-direction via capillary action. In examples in which the nonwoven web material includes or consists predominately or entirely of cotton fibers, for purposes of balancing priorities of absorbed fluid concealment and mechanical strength (needed for processing), versus limiting the quantity of topsheet material through which liquid must move in the z-direction to reach the absorbent structure beneath, it may be desired that the web have a basis weight of about 20 gsm to about 50 gsm, more preferably about 25 gsm to about 45 gsm, and even more preferably about 30 gsm to about 40 gsm. In conjunction, it may be desired that the web have a density of about 74 kg/m3 to about 110 kg/m3 and more preferably about 83 kg/m3 to about 101 kg/m3, where density is calculated as basis weight divided by caliper (z-direction thickness, measured using the caliper measurement method set forth below). Alternatively, or in combination with control of the values above, the caliper of the topsheet material may be controlled, to balance competing needs for opacity and loft (which call for a higher caliper) vs. a limitation on the z-direction distance that discharged fluid must travel through the topsheet from the wearer-facing surface to the outward-facing surface, to reach the absorbent structure below. Thus, it may be desired that the manufacture of the topsheet material be controlled to produce a topsheet material having a caliper of about 0.20 mm to about 0.60 mm, more preferably about 0.25 mm to about 0.55 mm, and even more preferably about 0.30 mm to about 0.45 mm. For purposes herein, caliper is measured using the caliper measurement method set forth below.

Immediately following separation from the bolls, cotton fiber is naturally hydrophobic due to the presence of natural waxy and oily compounds on the surfaces of the fibers. After ginning to separate the cotton fiber from the seeds, masses of raw cotton fiber (stored and transported in bales) typically include substantial quantities of impurities (particulates, bits of plant matter, etc.), trapped within the fibrous matrices and/or adhered to the waxes and oils, that both discolor the cotton fiber and make it unsuitable for many uses. In order to make raw cotton fiber commercially acceptable for most uses, the fiber must first be processed in several steps to remove the impurities. Typical processes also remove the natural waxes and oils and render the cotton fiber hydrophilic. Hydrophobizing agents such as oils, waxes or silicones can be reintroduced to render the cotton fibers and cotton-based fibrous structure hydrophobic and nonabsorbent, but for purposes herein an unapertured hydrophobic cotton-based topsheet would be unsuitable because it would not suitably accept and wick a discharge of fluid.

Following processing to remove impurities a mass of cotton fiber will be further mechanically processed to convert it to its intended end use condition and structure. Due to its hydrophilic nature, any mass of processed cotton fiber—whether appearing as a component of a textile/cloth, a paper product, a nonwoven web product or an absorbent product, will be absorbent of aqueous fluid to some extent, and will exhibit capillary wicking properties.

Rayon fiber is manufactured from regenerated cellulose. At a molecular level, it is chemically similar to cotton fiber. At the fiber level, rayon fiber can be imparted with complex surface geometry and substantial curl or crimp, and is naturally hydrophilic. A mass of rayon fiber will typically have absorbency properties exceeding those of an equal mass of cotton fiber.

Absorbency and wicking performance may vary according to, and may be manipulated by, the manner in which the fiber is further processed. Factors such as level of consolidation (i.e., densification) of the fiber mass in the end structure and orientations of the individual fibers within the end structure can affect absorbency and wicking performance.

Thus, for purposes contemplated herein, in combination with being imparted with a suitable basis weight, density and/or caliper as discussed above, it may be desired that a cotton- and/or rayon-based nonwoven web material used to make the topsheet 20 be formed via a nonwoven web manufacturing process in which substantial numbers of the fibers are imparted with directional orientation that includes some z-direction orientation, rather than orientations predominately biased along the machine direction or x-y plane of formation of the web structure. Following any suitable processes in which fibers are distributed and laid down in a batt on a horizontal forming belt (e.g., spunlaying, airlaying, wetlaying, carding, etc.), additional process steps that forcibly reorient some of the fibers or portions thereof in the z-direction may be employed. Suitable process steps may include, for example, needlepunching and hydroentangling. Hydroentangling, in which an array of fine, high-velocity water jets are directed at the batt as it is conveyed past them on a foraminous belt or drum, may be desired for its effectiveness in reorienting fibers while breaking fewer fibers and creating less broken fiber lint and surface fuzz (free fiber ends extending from the main structure of the web). A vacuum water removal system (in which air is drawn through the web in a z-direction into and through a pattern of orifices or pores on a drum or belt conveying the batt, pulling the hydrojetted water with it) may be desired because it tends to create, add, open and/or clear small z-direction passageways within the fiber matrix of the web, approximately in the pattern of the orifices or pores. Without intending to be bound by theory, it is believed that an increased number of fibers (or portions thereof) oriented in the z-direction, and the z-direction passageways, increase the ability and tendency of the web to wick aqueous fluid in the z-direction. In a topsheet, this would mean that the material can more readily wick aqueous fluid from the wearer-facing surface of the topsheet to the outward-facing surface of the topsheet, i.e., directly down to the absorbent structure below, and may thereby wick fluid less along x-y planar directions (causing a stain from discharged fluid to spread laterally and/or longitudinally).

For purposes herein, depending upon the extent of x-y plane deformation that is to be imparted as described herein, in some circumstances a nonwoven web precursor to the topsheet, formed partially or predominately, or even entirely, of continuous fibers (sometimes known as "filaments") spun from polymer resin and/or regenerated cellulose (rayon), may be preferred. (Herein, "continuous" fibers will be understood to be fibers that are not cut to staple length, but rather, are continuously spun and accumulated, without cutting or chopping, to form a batt on a moving forming belt in a continuous process. The batt is then consolidated and bonded (via, e.g., calendering and thermal compression spot bonding) to form a cohesive web. It will be understood that the fibers are not infinite in length, but generally will have varying indefinite lengths that are substantially greater than the length of a staple fiber. The process for forming such a web is sometimes known as a "spunbond" process and is described in the art.) Without intending to be bound by theory, it is believed that a spunbond web or topsheet formed therefrom may be better suited to the deformation process described herein, as it may permit deformation/plastic extension along the x-y plane, while better retaining cohesiveness and structural integrity, than a web formed predominately of staple fibers and/or natural plant fibers such as cotton, of shorter lengths.

Absorbent Structure

The absorbent structure 40 of the present disclosure may be imparted with any suitable shape including, but not limited to, an oval, a discorectangle, a rectangle, an asymmetric shape, and an hourglass. For example, in some configurations, the absorbent structure 40 may have a contoured shape, e.g., narrower in the intermediate region than in the end regions. As yet another example, the absorbent structure may comprise a tapered shape having a wider portion in one end region of the pad which tapers to a narrower end region in the other end region of the pad. Where the article is an absorbent pad intended for use by a woman, it may be desired that the rearward end region be wider and the forward end region be narrower. Where the article is an absorbent pad intended for use by a man, it may be desired that the rearward end region be narrower and the forward end region be wider. The absorbent structure 40 may comprise varying stiffnesses in the longitudinal and lateral directions.

The configuration and construction of the absorbent structure 40 may vary (e.g., the absorbent structure 40 may have varying caliper zones, a hydrophilic gradient, a superabsorbent gradient, or lower average density and lower average basis weight acquisition zones). Further, the size and absorbent capacity of the absorbent structure 40 may also be varied to accommodate a variety of wearers. However, the total absorbent capacity of the absorbent structure 40 should be compatible with the design loading and the intended use of the absorbent article.

In some forms, the absorbent structure 40 may include a plurality of multi-functional layers. For example, the absorbent structure 40 may include a core wrap (not shown) useful for enveloping other layers. The core wrap may be formed by one or two sections of nonwoven material, substrates, laminates, films, or other materials. In some examples, the core wrap may be formed of a single material, or laminate, wrapped at least partially around itself.

The absorbent structure 40 may include one or more adhesives, for example, to help immobilize absorbent gelling material/superabsorbent polymer (SAP) or other absorbent materials included within the absorbent structure.

Absorbent structures comprising relatively high amounts of SAP with various absorbent structure/core designs are disclosed in U.S. Pat. No. 5,599,335; EP 1,447,066; WO 95/11652; US 2008/0312622A1 to Hundorf et al.; and WO 2012/052172. These may be used to configure the superabsorbent layers.

Additions to the absorbent structure of the present disclosure are envisioned. In particular, potential additions to the current multi-laminate absorbent structure are described in U.S. Pat. Nos. 4,610,678; 4,673,402; 4,888,231; and 4,834,735. The absorbent structure may further comprise additional layers that mimic the dual core system containing an acquisition/distribution structure of chemically stiffened fibers positioned over an absorbent structure as detailed in U.S. Pat. No. 5,234,423; and in U.S. Pat. No. 5,147,345. These are useful to the extent they do not negate or conflict with the effects of the below described laminates of the absorbent structure of the present invention.

Some examples of suitable absorbent structures 40 that can be used in the absorbent article of the present disclosure are described in US 2018/0098893 and US 2018/0098891. Examples of possible suitable configurations are further described and depicted in U.S. application Ser. No. 16/831,851.

In some configurations, the absorbent structure 40 may be formed of or include a layer of absorbent open-celled foam material. In some examples, the foam material may include at least first and second sublayers (e.g., 40*t*, 40*b*, see FIG. 4D) of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below.

The open-celled foam material may be a foam material that is manufactured via polymerization of the continuous oily monomer phase of a water-in-oil high internal phase emulsion ("HIPE"). A HIPE for purposes herein is a two-phase water-in-oil emulsion in which the water-to-oil ratio is greater than about 2.85:1, i.e., about 74 percent aqueous/dispersed phase (by volume). Due to this relatively high ratio of aqueous phase to oil phase, upon emulsification sufficient to result in a foam of the type contemplated herein (i.e., average cell size 1 to 300 micrometers), the dispersed aqueous phase will have the form of droplets forced into polyhedral forms as a result of close crowding, separated by thin film walls formed of the oil/continuous phase. An example of such an open-celled HIPE foam material is found in the absorbent structures of ALWAYS INFINITY brand feminine hygiene pads currently manufactured and marketed by The Procter & Gamble Company, Cincinnati, Ohio. An open-celled foam material as described herein may be preferred for purposes herein, because it may be manufactured to be relatively brittle under tension, such that it can be caused to fracture neatly along orderly lines to form approximately or substantially uniformly sized and shaped pieces, in the deformation process described herein.

The oil phase of a HIPE is continuous and includes monomers to be polymerized, and an emulsifier to help create and stabilize the HIPE. The oil phase may also include one or more photoinitiators. The monomer component may be included in an amount of from about 80% to about 99%, and in certain examples from about 85% to about 95% by weight of the oil phase. The emulsifier component, which is soluble in the oil phase and suitable for forming a stable water-in-oil emulsion may be included in the oil phase in an amount of from about 1% to about 20% by weight of the oil phase. The emulsion may be formed at an emulsification temperature of from about 20° C. to about 130° C. and in certain examples from about 50° C. to about 100° C.

In general, the monomers may be included in an amount of about 20% to about 97% by weight of the oil phase and may include at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also include from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain examples from about 2% to about 8%, to modify properties of the HIPE foams. In certain cases, "toughening" monomers may be desired to impart toughness to the resulting HIPE foam. These include monomers such as styrene, vinyl chloride, vinylidene chloride, isoprene, and chloroprene. Without intending to be bound by theory, it is believed that such monomers aid in stabilizing the HIPE during polymerization (also known as "curing") to provide a more homogeneous and better-formed HIPE foam which results in greater toughness, tensile strength, abrasion resistance, and the like. Monomers may also be added to confer flame retardancy, as disclosed, for example, in U.S. Pat. No. 6,160,028. Monomers may be added to impart color (for example vinyl ferrocene); to impart fluorescent properties; to impart radiation resistance; to impart opacity to radiation (for example lead tetraacrylate); to disperse charge; to reflect incident infrared light; to absorb radio waves; to make surfaces of the HIPE foam struts or cell walls wettable; or for any other desired property in a HIPE foam. In some cases, these additional monomers may slow the overall process of conversion of HIPE to HIPE foam, the tradeoff being necessary if the desired property is to be conferred. Thus, such monomers can also be used to slow down the polymerization rate of a HIPE. Examples of monomers of this type comprise styrene and vinyl chloride.

The oil phase may further include an emulsifier to facilitate emulsification and stabilize the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they constitute about 1% to about 20%, in certain examples about 2% to about 15%, and in certain other examples about 3% to about 12%, of the weight of the oil phase. In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Any photoinitiators included may be included at between about 0.05% and about 10%, and in some examples between about 0.2% and about 10% by weight of the oil phase. Lower amounts of photoinitiator allow light to better penetrate the HIPE foam, which can provide for polymerization deeper into the HIPE foam. However, if polymerization is performed in an oxygen-containing environment, it may be desired that there be enough photoinitiator present to initiate the polymerization and overcome oxygen inhibition. Photoinitiators can respond rapidly and efficiently to a light source with the production of radicals, cations, and other species that are capable of initiating a polymerization reaction. Photoinitiators selected for use in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Specialty Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Specialty Chemicals as DAROCUR® 1173); 2-methyl-1-[4-(methyl thio)phenyl]-2-morpholino-propan-1-one (sold by Ciba Specialty Chemicals as IRGACURE® 907); 1-hydroxycyclohexyl-phenyl ketone (sold by Ciba Specialty Chemicals as IRGACURE® 184); bis(2,4,6-trimethylbenzoyl)-phenylphosphineoxide (sold by Ciba Specialty Chemicals as IRGACURE 819); diethoxyacetophenone, and 4-(2-hydroxyethoxy)phenyl-(2-hydroxy-2-methylpropyl) ketone (sold by Ciba Specialty Chemicals as IRGACURE® 2959); and Oligo [2-hydroxy-2-methyl-1-[4-(1-methylvinyl)phenyl]propanone] (sold by Lamberti spa, Gallarate, Italy as ESACURE® KIP EM.

The dispersed aqueous phase of a HIPE includes predominately water, and may also include one or more components, such as initiator, photoinitiator, or electrolyte, wherein in certain examples, the one or more components are at least partially water soluble.

One component included in the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be included in the aqueous phase is a water-soluble free-radical initiator. The initiator can be present at up to about 20 mole percent based on the total moles of polymerizable monomers present in the oil phase. In certain examples, the initiator may be included in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, azo initiators, redox couples like persulfate-bisulfate, persulfate-ascorbic acid, and other suitable redox initiators. In certain examples, to reduce the potential for premature polymerization which may clog the emulsification system, addition of the initiator to the monomer phase may be performed near the end of the emulsification step, or shortly afterward.

Photoinitiator, if included in the aqueous phase, may be at least partially water soluble, and may constitute between about 0.05% and about 10%, and in certain examples between about 0.2% and about 10%, by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. Photoinitiators selected for use to form foams within contemplation of the present disclosure may absorb UV light at wavelengths of from about 200 nanometers (nm) to about 800 nm, in certain examples from about 200 nm to about 350 nm, and in certain examples from about 350 nm to about 450 nm. If a photoinitiator is to be included in the aqueous phase, suitable types of water-soluble photoinitiators may include benzophenones, benzils, and thioxanthones. Examples of photoinitiators include 2,2'-Azobis[2-(2-imidazolin-2-yl) propane]dihydrochloride; 2,2'-Azobis[2-(2-imidazolin-2-yl) propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components, other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain examples, a HIPE foam layer may be manufactured so as to have one or more sublayers (e.g., 40*t*, 40*b*, see FIG. 4D), and may be either homogeneous or heterogeneous polymeric open-celled foams. Homogeneity and heterogeneity relate to distinct layers within the same HIPE foam, which are similar in the case of homogeneous HIPE foams and differ in the case of heterogeneous HIPE foams. A heterogeneous HIPE foam may contain at least two distinct sublayers that differ with regard to their chemical composition, physical properties, or both; for example, sublayers may differ with regard to one or more of foam density, polymer composition, specific surface area, or pore size (also referred to as cell size). For example, for a HIPE foam if the difference relates to pore size, the average pore size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cm$^3$, another layer may have a density of at least about 0.024 g/cm$^3$ or less than about 0.016 g/cm$^3$, in certain examples at least about 0.027 g/cm$^3$ or less than about 0.013 g/cm$^3$, and in still other examples at least about 0.030 g/cm$^3$ or less than about 0.010 g/cm$^3$. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation, another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam layer comprising first and second foam sublayers, wherein the first foam sublayer has a relatively larger pore or cell size, than the second sublayer, when used in an absorbent article may more quickly absorb incoming fluids than the second sublayer. For example, when the HIPE foam layer is used to form an absorbent structure of a feminine hygiene pad, the first foam sublayer may be layered over the second foam sublayer having relatively smaller pore sizes, as compared to the first foam sublayer, which exert more capillary pressure and draw the acquired fluid from the first foam sublayer, restoring the first foam sublayer's ability to acquire more fluid from above.

HIPE foam pore sizes may range from about 1 to about 200 μm and in certain examples may be less than about 100 μm. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer. An example of an open-celled HIPE foam layer having two sublayers is found in the absorbent structures of ALWAYS INFINITY brand feminine hygiene pads currently manufactured and marketed by The Procter & Gamble Company, Cincinnati, Ohio.

The HIPE foam layers of the present disclosure are relatively open-celled. This refers to the individual cells or pores of the HIPE foam layer being in substantially unobstructed fluid communication with adjoining cells. The cells in such substantially open-celled HIPE foam structures have intercellular openings or windows that are large enough to permit ready fluid transfer from one cell to another within the HIPE foam structure. For purpose of the present disclosure, a HIPE foam is considered "open-celled" if at least about 80% of the cells in the HIPE foam that are at least 1 μm in size are in fluid communication with at least one adjoining cell.

In addition to being open-celled, in certain examples HIPE foams are adapted to be sufficiently hydrophilic to permit the HIPE foam to absorb aqueous fluids. In some examples the internal surfaces of a HIPE foam may be rendered hydrophilic by residual hydrophilizing surfactants or salts left in the HIPE foam following polymerization, or by selected post-polymerization HIPE foam treatment procedures such as those as described in references cited herein.

In some configurations, for example when it is used to form an absorbent structure of a feminine hygiene pad, a HIPE foam layer may be flexible and exhibit an appropriate glass transition temperature (Tg). The Tg represents the midpoint of the transition between the glassy and rubbery states of the polymer. In general, HIPE foams that have a Tg that is higher than the temperature of use can be strong but will also be relatively rigid and potentially prone to fracture (brittle). In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions; in certain other examples Tg will be less than about 30° C. For HIPE foams used in applications wherein the use temperature is higher or lower than ambient temperature, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent structures and/or sublayers within contemplation of the present disclosure, and materials and methods for their manufacture, also include but are not necessarily limited to those foams and methods described in U.S. Pat. Nos. 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; and US 2011/0160689, which are incorporated herein by reference to the extent not inconsistent herewith.

Figure 2:
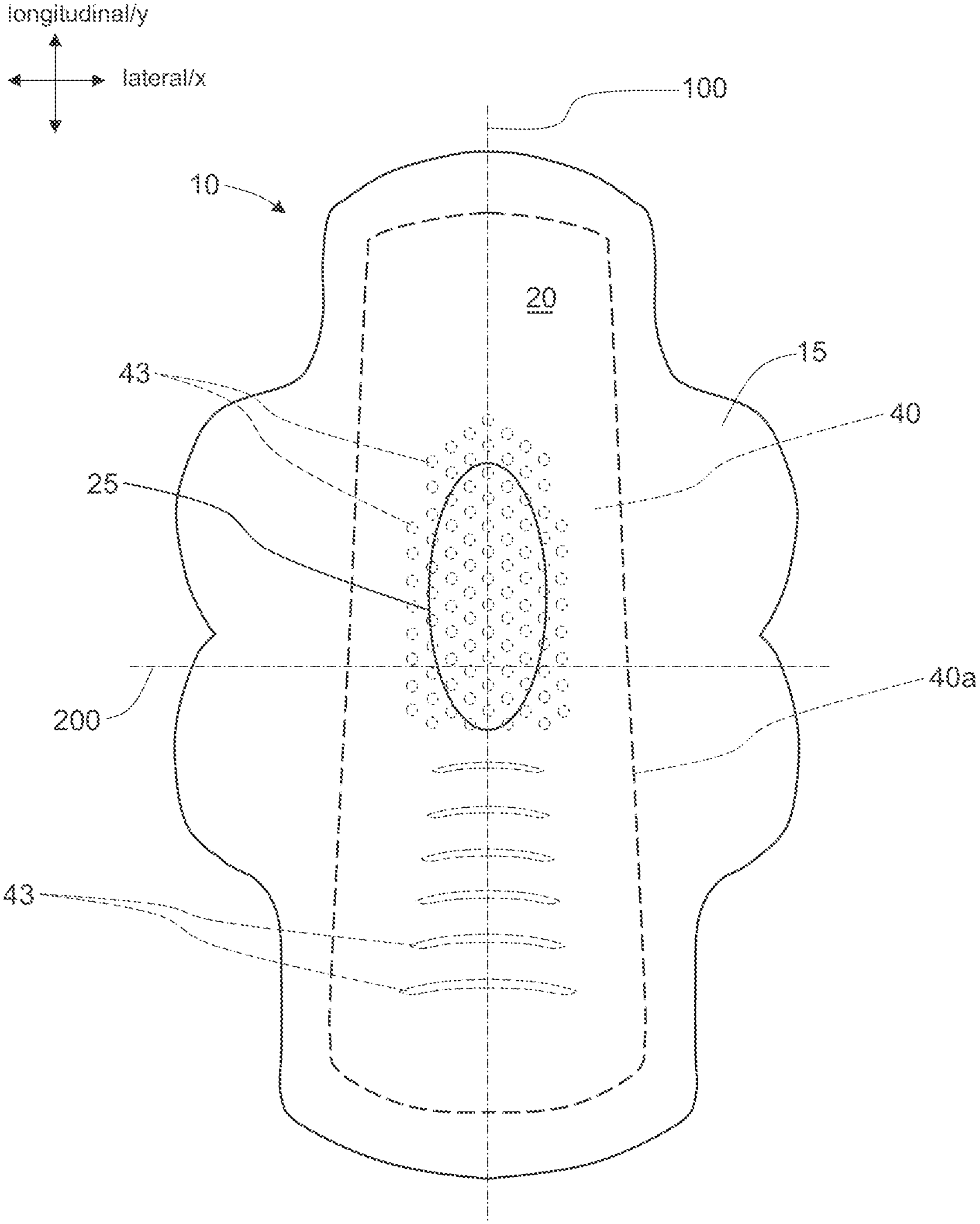
FIG. 2 is a plan view of an example of an absorbent article in the form of a feminine hygiene pad, wearer-facing side up, illustrating various other features.

As reflected in FIG. 2, an absorbent structure 40 formed of HIPE foam may include one or more patterns of apertures 43, including at least a first pattern disposed within an expected discharge location overlying the intersection of longitudinal and lateral axes 100, 200 of the pad. Apertures 43 may be punched, cut or otherwise formed through the entire z-direction depth of the HIPE foam absorbent structure, or only through a wearer-facing layer or partially into the wearer-facing portion thereof. When a HIPE foam absorbent structure is disposed in direct contact with a topsheet as described herein, with no intervening acquisition layer formed of another material, apertures 43 may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such apertures help decrease bending stiffness of the absorbent structure, which may help increase comfort of the pad for the wearer. A pattern of apertures having an average radius or other largest dimension of 1.0 mm to 4.0 mm, and more preferably 1.5 mm to 3.5 mm may be included, within, for example, the area occupied by the bonding region 25. The pattern may include apertures at a numerical density of 3.0 to 9.0 apertures per $cm^2$, and more preferably 4.0 to 8.0 apertures per $cm^2$. In selecting the appropriate average size, numerical density, and surface area occupied by the pattern of apertures, the manufacturer may wish to balance the volume of the "reservoirs" desired with the need to retain absorbent material in locations proximate to and about the expected discharge location. Additional details concerning configurations of such apertures in combination with examples of suitable absorbent structures may be found in U.S. Pat. No. 8,211,078.

The absorbent structure 40 formed of HIPE foam should be imparted with sufficient capillary work potential in absorption mode (CWPA) (described below) to have capability to effectively draw discharged fluid from a topsheet over a time of use/wear of the pad during menstruation that is normal and expected for feminine hygiene pads, for example, from 4 to 8 hours. As noted below, the CWPA of a material is in part affected by its volume. Thus, it may be desired that an absorbent structure 40 formed of HIPE foam have a caliper (prior to wetting) that provides satisfactory volume to a standard-sized pad. Of course, a relatively thick pad can be manufactured, but that is typically deemed undesirable for daytime use in view of desires for flexibility/pliability and thinness, for comfort and discreetness under clothing. The manufacture must balance these competing objectives. Accordingly a feminine hygiene pad with a HIPE foam absorbent structure as contemplated herein, it may be desired that the layer have a caliper in the majority of its wearer-facing surface area (prior to wetting) of about 1 mm to about 5 mm, or more preferably about 1.5 mm to about 3.5 mm, or even more preferably about 2.0 mm to about 3.0 mm.

(The caliper of a HIPE foam layer may be measured visually, with assistance of magnification/microscopy and/or photography or any other facilitating techniques and equipment, to any extent deemed useful.) Where the absorbent structure 40 includes two sublayers as described herein, it may be desired that an upper sublayer 40*t* have a caliper (prior to wetting) of about 0.64 mm to about 3.2 mm, or preferably about 0.96 mm to about 2.24 mm, or even more preferably about 1.28 mm to about 1.92 mm; and it may be desired that a lower sublayer 40*b* have a caliper (prior to wetting) of about 0.16 mm to about 0.80 mm, or more preferably about 0.24 mm to about 0.56 mm, or even more preferably about 0.32 mm to about 0.48 mm.

In some configurations, the absorbent structure 40 may consist of or include a heterogeneous layer consisting of an absorbent foam material (such as a HIPE foam material, as described above) with structure that has been polymerized and thereby formed about, among and/or within the matrix of fibers of a nonwoven web material. Examples of such heterogeneous layers are depicted and described in US2017/0119587; US2017/0119596; US2017/0119597; US2017/0119588; US2017/0119593; US2017/0119594; US2017/0119595; and US2017/0199598.

Absorbency Properties and Interface Between Topsheet and Absorbent Structure

The affinity and absorbency of an absorbent/hydrophilic structure for an aqueous fluid may be characterized in part by its capillary absorption pressure. Capillary absorption pressure (CAP) may be measured according to steps in the Capillary Work Potential measurement method set forth below. It is a value that reflects the magnitude of the tendency of the structure to draw in aqueous fluid. It will be appreciated that a plot of the CAP of an absorbent structure vs. saturation level will have an initial maximum value (at the outset of absorption of fluid) and decrease as the structure draws in fluid and approaches its full absorption capacity, i.e., full saturation.

The resistance to desorption, or the tendency of an absorbent/hydrophilic structure to retain absorbed fluid, may be characterized in part by its capillary desorption pressure (CDP). CDP, which also may be measured according to steps in the Capillary Work Potential measurement method set forth below, is a value that reflects the magnitude of pressure (or pressure differential) required to drive (or draw) out aqueous fluid absorbed and held in the structure. It will be appreciated that a plot of the CDP of a structure vs. saturation level will have an initial minimum value (prior to exit of any fluid from the structure), and increase as the fluid leaves it.

CAP and CDP of a given structure are a function of the extent of hydrophilicity of the solid surfaces within the structure, the average size of the interstitial spaces or voids, cells or pores within the structure among/between the solid surfaces, and the number of the interstitial spaces, cells or pores within the structure per unit volume of the structure.

In order for a layered topsheet/absorbent structure combination to be able to effectively move discharged fluid from the top surface of the topsheet in a z-direction direction away from the wearer, in addition to other conditions described herein, the CAP of the absorbent structure must be greater than the CDP of the topsheet, at a selected level of absorbed fluid content of the topsheet, preferably a relatively low level. In order for a layered topsheet/absorbent structure combination to be able to move discharged fluid in a z-direction direction away from the wearer with acceptable rapidity, i.e., such that the topsheet does not have time to excessively wick and thereby distribute (i.e. spread) discharged fluid along x-y planar directions (creating an undesirably large stain on the topsheet) and does not feel overly wet to the wearer shortly following a discharge of fluid thereon, the capillary absorption pressure of the absorbent structure at, e.g., a 20 percent saturation should be greater than the capillary desorption pressure of the topsheet at the same saturation, where percent saturation is the percent of total pore volume of the material that is occupied by the fluid, and the test fluid is saline solution as specified in the Capillary Work Potential measurement method set forth below.

The total absorbency of a given material structure may be further characterized by its capillary work potential in absorption mode (CWPA) and drainage or desorption mode (CWPD), as measured using the Capillary Work Potential measurement method set forth below. CWPA is a measure of the work that an absorbent material will perform in drawing in a quantity of aqueous fluid under conditions of the described method. CWPD is a measure of the work necessary to expel or draw away aqueous fluid absorbed and held by a structure under conditions of the described method. For a given structure that is hydrophilic and absorbent of aqueous fluid, the CWPD will be greater than the CWPA because the properties of an absorbent structure (hydrophilicity; cell/pore size and volume) cause it to tend to retain fluid. CWPA and CWPD of a given structure are affected by the features and properties that affect CAP and CDP, and also by the total volume of the interstitial spaces or voids, cells or pores within the structure within the structure. Thus, it will be appreciated that CWPA and CWPD of a structure are in part affected by the total volume (i.e., size) of the structure.

In order to ensure that the absorbent structure 40 will drain the topsheet 20 of fluid absorbed by the topsheet sufficiently for the two to provide a satisfactory pad, the absorbent structure 40 should have a CWPA that is greater than the CWPD of the topsheet. If this condition is not satisfied, the absorbent structure will not sufficiently drain fluid from the topsheet to both (1) ensure that the topsheet will not retain an unacceptably wet feeling following a discharge; and (2) ensure that the topsheet is kept drained and has capacity to accept successive discharges of fluid over a reasonable time of use of the article 10.

It has been learned that an absorbent structure formed of HIPE foam as described herein may be manufactured to have a capillary absorption pressure great enough to draw fluid from an absorbent cotton topsheet with acceptable rapidity over repeated discharges, i.e., over a reasonable time of use of the pad.

In examples in which the topsheet is formed in part or in whole of web material including hydrophilic fibers, the topsheet material may tend to retain fluid on its wearer-facing and outward-facing surfaces, and within the interstitial spaces between and along the surfaces of the fibers within the web material, unless the underlying material has absorption capacity and absorption pressure greater than the desorption pressure of the topsheet, as described above; and there is sufficient direct contact maintained between the topsheet and the underlying absorbent structure to enable the fluid to move from fiber surfaces within the topsheet structure, directly to surfaces of material within the underlying absorbent structure, such that the underlying absorbent structure may draw the fluid from the topsheet. Prior to the time it is fully saturated, an absorbent material will tend not to release absorbed fluid unless an adjacent material with greater affinity for the fluid is in sufficient direct contact. Accordingly, it is important to provide structure sufficient to maintain sufficient contact, without obstructing fluid movement. No intervening layer or structure of material, or at least no intervening layer or structure of material less absorbent than the topsheet or more absorbent than the absorbent structure, should be interposed between the material of the topsheet 20 and the material of the absorbent structure 40, at least within the bonding region 25, more preferably over a majority of the wearer-facing surface area of the absorbent structure 40, and even more preferably over the entirety of the wearer-facing surface area of the absorbent structure 40—unlike systems provided in many current feminine hygiene pads, which include a distinct fluid acquisition/distribution material layer between the topsheet and the absorbent materials of the absorbent structure.

In some examples, sufficient direct contact between the topsheet 20 and the absorbent structure 40 may be effected by deposit(s) of adhesive between the topsheet 20 and the absorbent structure 40, adhesively bonding them in close z-direction proximity. The adhesive may be applied in a pattern or arrangement of adhesive deposits interspersed with areas in which no adhesive is present (unbonded areas), such that the adhesive holds the two layers in close z-direction proximity, while areas remain in which no adhesive is present to obstruct z-direction fluid movement between the layers.

Referring to FIG. 2, to ensure that the topsheet 20 and absorbent structure 40 are held in sufficiently close z-direction proximity at least in the area of the topsheet 20 expected to receive a discharge of fluid, it may be desired to dispose a bonding region 25 on the pad at a location that includes the intersection of the longitudinal and lateral axes 100, 200. The bonding region 25 should be of sufficient size to be reliably present beneath the expected discharge location when the pad is in use, with reasonably minor variations of placement by the wearer within the underpants; accordingly, it may be desired that the bonding region have an area of at least about 15 $cm^2$, more preferably at least about 30 $cm^2$. Even more preferably, it may be desired that the bonding region 25 have an area that is at least half of the total wearer-facing surface area of the absorbent structure 40 (within its perimeter 40*a*). (Note: FIG. 2 is not presented herein as actual size or scale depiction.)

Figure 3A:
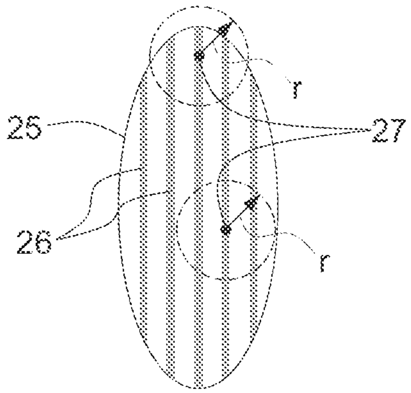
FIGS. 3A-3C are schematic plan views of several possible non-limiting examples of patterns of arrangements of bonding regions between a topsheet and underlying components of an absorbent article.
Figure 3B:
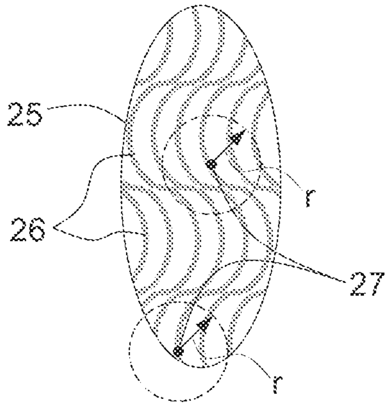
Figure 3C:
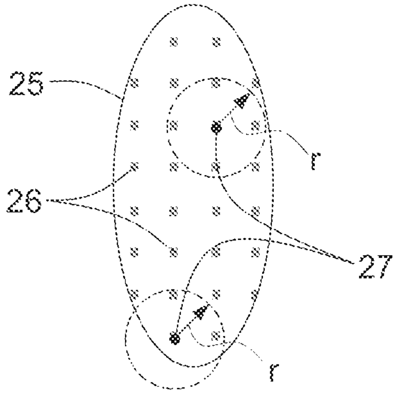

Referring to FIGS. 2-3C, to ensure that the topsheet 20 and the absorbent structure 40 remain in sufficient z-direction proximity during use, it may be desired that, within any identifiable first point location of bonding 27 within the bonding region 25, at which the topsheet is bonded to the absorbent structure, there is a second identifiable point location at which the topsheet is bonded to the absorbent structure, within an about 10 mm radius, more preferably within an about 6 mm radius, about 5 mm radius, about 4 mm radius, and even more preferably with an about 3 mm radius r of the first point location. Referring to FIGS. 3A-3C, depicting three non-limiting examples, it can be seen that a variety of patterns or arrangements of bonds (via adhesive deposits 26 or other bonding mechanisms) may be employed to impart this feature. Within radius r of each identifiable point location of bonding 27, there are a number of additional point locations where bonding between the topsheet and the absorbent structure is present in the examples depicted.

It will be appreciated that a continuous film- or coating-like deposit of adhesive may be applied to bond the topsheet and the absorbent structure within the entirety of bonded region 25, but that such a continuous deposit of adhesive could form an occlusive barrier that would obstruct the movement of fluid from the topsheet and into the absorbent structure. Accordingly, it is preferable that, in examples in which the bonding mechanism is deposits of adhesive, the deposits are disposed in a pattern or arrangement that is discontinuous or intermittent such that it creates bonded areas interspersed with unbonded areas between the topsheet and the absorbent structure, as suggested in FIGS. 3A-3C.

Figure 3D:
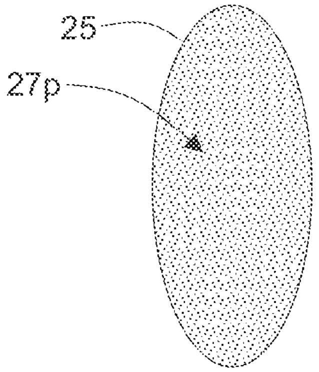
FIG. 3D is a schematic plan view of another possible example of a pattern of adhesive deposit to form a bonding region between a topsheet and underlying components of an absorbent structure.

In another example suggested in FIG. 3D, a dense arrangement of relatively small point bond locations may be effected by spraying suitable adhesive onto one or both of the outward-facing surface of the topsheet 20 and the wearer-facing surface of the absorbent structure in contact with the outward-facing surface of the topsheet. If the adhesive suitably adapted (e.g. its viscosity), the spray nozzle is suitably configured, and the rate of spray (liquid volume or weight of adhesive sprayed/time/surface area of spray coverage) is suitably regulated, such that discrete spray droplets strike and adhere to the surface in discrete locations, to an extent suitably limited such that a continuous deposit or continuous film is not formed, the sprayed adhesive can form a dense random pattern 27*p* of discrete point bonding locations that falls within the description in the preceding paragraph hereinabove, but does not result in a continuous film of deposited adhesive that occludes pores of the underlying absorbent structure or obstruct the movement of fluid from the topsheet to the underlying absorbent structure.

Additionally, when the absorbent structure is formed of an open-celled foam (such as a HIPE foam contemplated herein) it may be desired that the adhesive selected not effect adhesion to the absorbent structure via chemical, dispersive or diffusive adhesion with the foam layer at the adhesive deposit locations, but rather, that it effect adhesion to the foam layer mechanically, by flowing to a limited extent into the cells, at least partially assuming the shapes thereof, and solidifying in such position to form mechanical interlocks with the cell structures, which enable the adhesive to hold the topsheet and/or backsheet to the absorbent structure. Such an adhesive may be preferred so as not to alter the molecular structure or composition of the foam material, potentially negatively affecting its fluid absorption properties or mechanical strength. In some configurations, a portion of the adhesive may penetrate into the wearer-facing surface of the foam material and into the garment-facing surface of the topsheet and/or a portion of the adhesive may penetrate into the garment-facing surface of the foam material and into the wearer-facing surface of the backsheet to bond the foam material to the topsheet and/or backsheet. One suitable example may be an adhesive of the designation H2031-05X, a product of Bostik, a division or subsidiary of the Arkema Group, Columbes, France.

Backsheet

The backsheet 30 may be positioned beneath or subjacent an outward-facing surface of the absorbent structure 40 and may be joined thereto by any suitable attachment methods. For example, the backsheet 30 may be secured to the absorbent structure 40 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In some configurations, it is contemplated that the absorbent structure 40 is not joined directly to the backsheet 30.

The backsheet 30 may be impermeable or substantially impermeable by aqueous liquids (e.g., urine, menstrual fluid) and may be manufactured from a thin plastic film, although other flexible liquid impermeable materials may also be used. As used herein, the term "flexible" refers to materials which are compliant and will readily conform to the general shape and contours of the human body. The backsheet 30 may prevent, or at least substantially inhibit, fluids absorbed and contained within the absorbent structure 40 from escaping and reaching articles of the wearer's clothing which may contact the pad 10, such as underpants and outer clothing. However, in some instances, the backsheet 30 may be made and/or adapted to permit vapor to escape from the absorbent structure 40 (i.e., the backsheet is made to be breathable), while in other instances the backsheet 30 may be made so as not to permit vapors to escape (i.e., it is made to be non-breathable). Thus, the backsheet 30 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of materials suitable for forming a backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523; 3,989,867; 3,156,242; WO 97/24097; U.S. Pat. Nos. 6,623,464; 6,664,439 and 6,436,508.

The backsheet 30 may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881,489; 4,341,216; 4,713,068; 4,818,600; EP 203 821; EP 710 471; EP 710 472; and EP 0 793 952.

For purposes described herein, it may be preferred that a film from which the backsheet is to be formed be formed of component material(s) (e.g., polymer resin(s)) to yield a film that exhibits suitable plastic deformability/extensibility, such that it may be locally plastically stretched along x-y plane directions (to a limited extent) without failure or rupture, along discrete locations, by passage through deforming rollers as described herein. Thermoplastic resins identified above expressly or by reference are deemed potential non-limiting examples suitable for such purpose.

Suitable backsheet materials may have a basis weight of from about 20 gsm to about 28 10 gsm, or from about 22 gsm to about 25 gsm. It was surprisingly found that absorbent articles described herein having a backsheet with a basis weight of less than 20 gsm may be too thin in the plastically stretched zones, resulting in the backsheet having a sheer appearance that may be undesirable to some consumers.

Mechanical Processing

It has been learned that mechanically processing at least the absorbent structure 40, or the absorbent structure together with one or both the topsheet 20 and backsheet 30, in the manner described herein, can provide a number of unexpected benefits.

Figure 10:
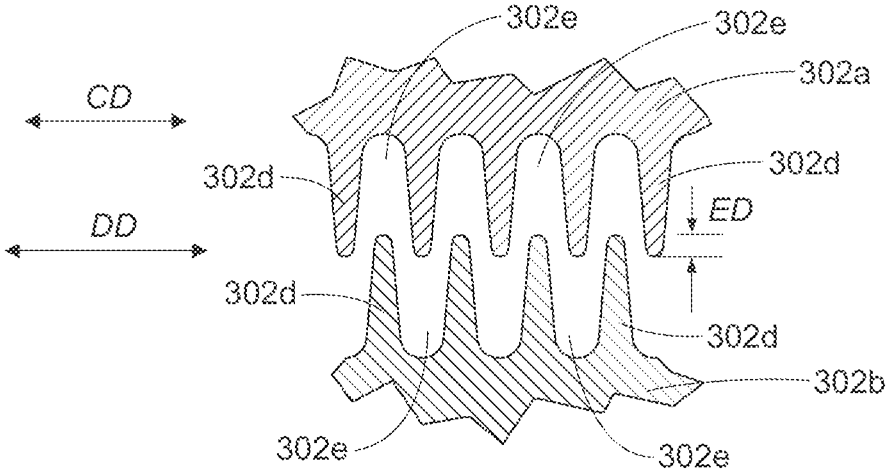
FIG. 10 is a view of engaging features of portions of an example of a pair of deforming rollers.
Figure 11:
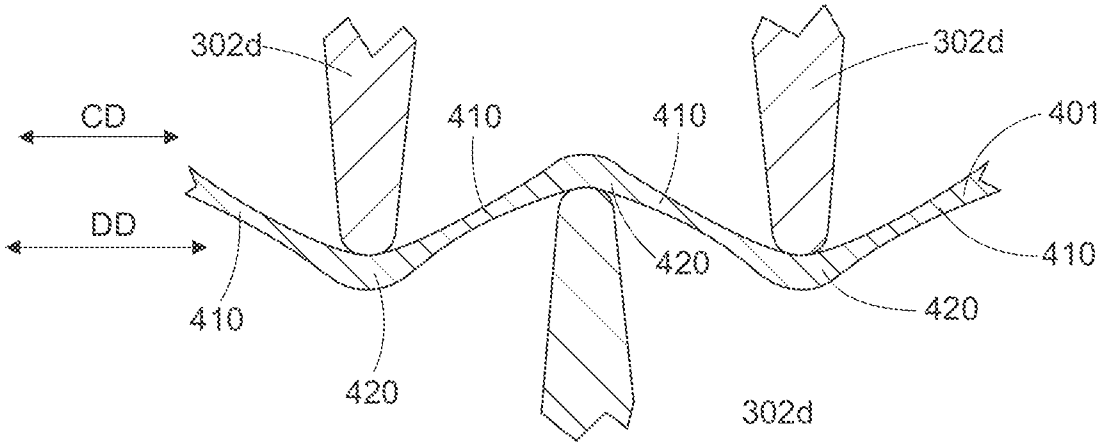
FIG. 11 is a closer view of the features shown in FIG. 10, shown acting upon a web.
Figure 12:
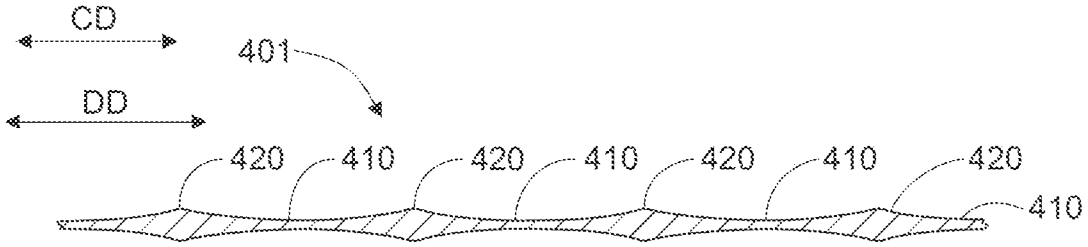
FIG. 12 is a schematic cross section view (along a z-direction plane) of an example of a deformed web.
Figure 13:
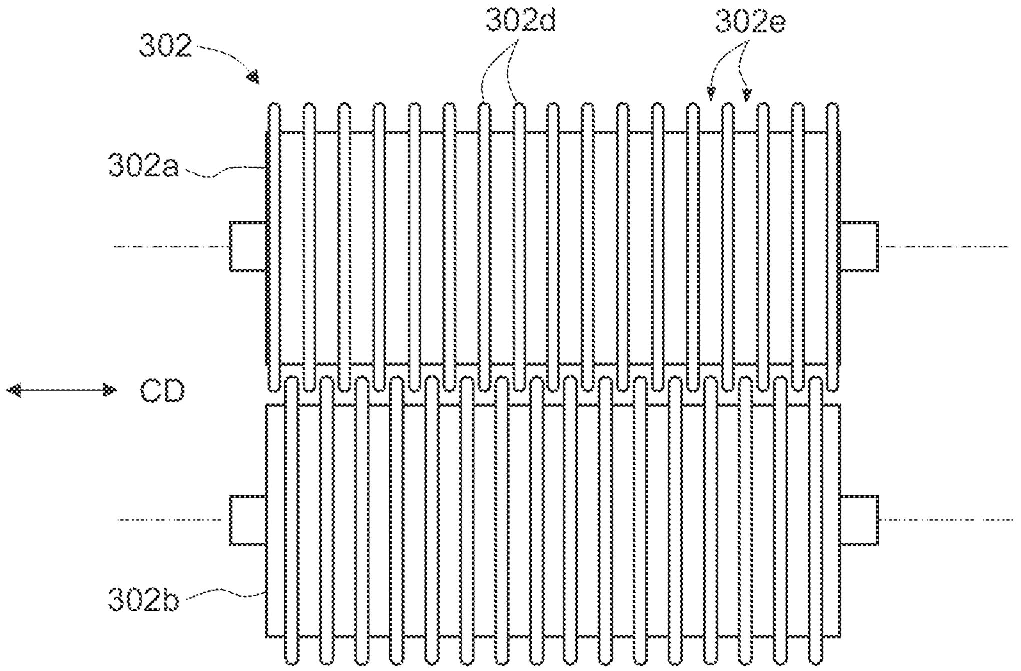
FIG. 13 is a view along the machine direction, of another example of a pair of deforming rollers.

A process known as "incremental stretching" involves passing a web through a nip between a pair of rollers, the rollers having mating features that cause discrete, incremental sections of the web to be stretched across lines coincident with features of the rollers. Non-limiting examples of incremental stretching processes and equipment are disclosed in U.S. Pat. No. 6,383,431. It has been learned that this process may be applied to not only a single web layer, but a composite web of a plurality of layers including components of an absorbent structure, to beneficial effect. Referring to FIGS. 8-13, for example, mating rollers 302*a*, 302*b* may be provided with respective circumferential ridges 302*d* separated by circumferential grooves 302*e*. The rollers may be configured such that the ridges of one engage with the grooves of the other to a desired engagement depth ED (FIG. 10). Upon passage of a layered composite web 400 being conveyed along a machine direction MD through a nip 302*c* between the engaged rollers, it will be stretched along a cross direction CD as it is forced to bend over the respective ridges 302*d* of each roller. If the engagement depth ED is suitably adjusted, one or more layer components of the composite web 400 can be caused to stretch beyond their yield points, to plastic deformation or even fracture, along machine direction lines, as the web 400 passes through the nip, resulting in a deformed composite web 401. (The roller configuration reflected in FIGS. 9-11 and 13 is sometimes known as a "ring rolling" configuration, or "ring rollers.") Resulting less deformed, or undeformed, zones 420, and more-deformed zones 410 of this potential CD deformation or fracture in layer components of web 401 are schematically depicted in FIGS. 11 and 12. In configuration shown in FIGS. 10 and 11, the direction of stretch deformation DD is aligned or substantially parallel with the cross direction CD.

Figure 14:
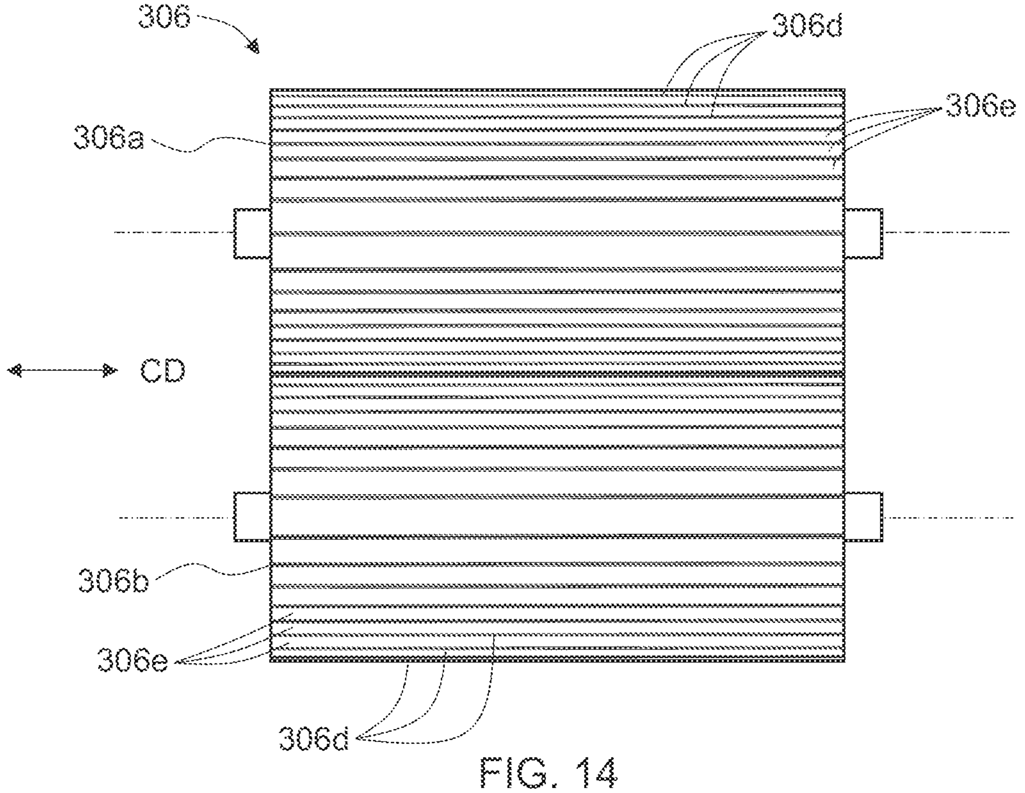
FIG. 14 is a view along the machine direction, of another example of a pair of deforming rollers.
Figure 15A:
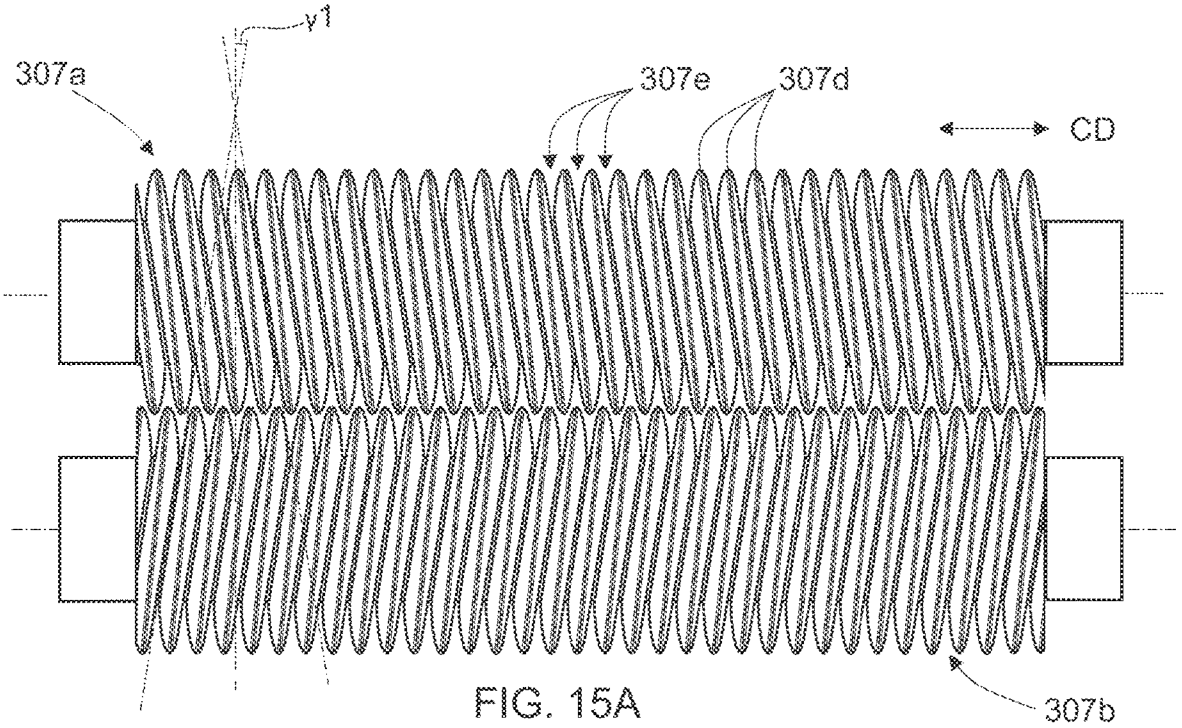
FIG. 15A is a view along the machine direction, of another example of a pair of deforming rollers.
Figure 15B:
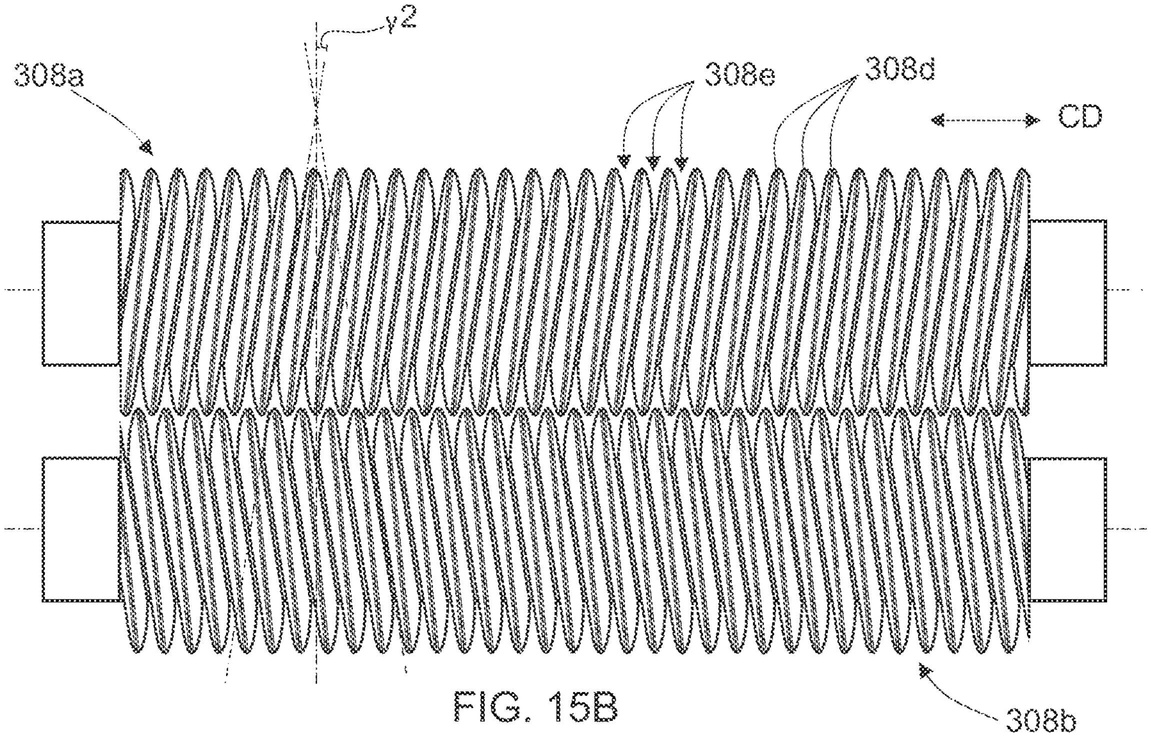
FIG. 15B is a view along the machine direction, of another example of a pair of deforming rollers.
Figure 16A:
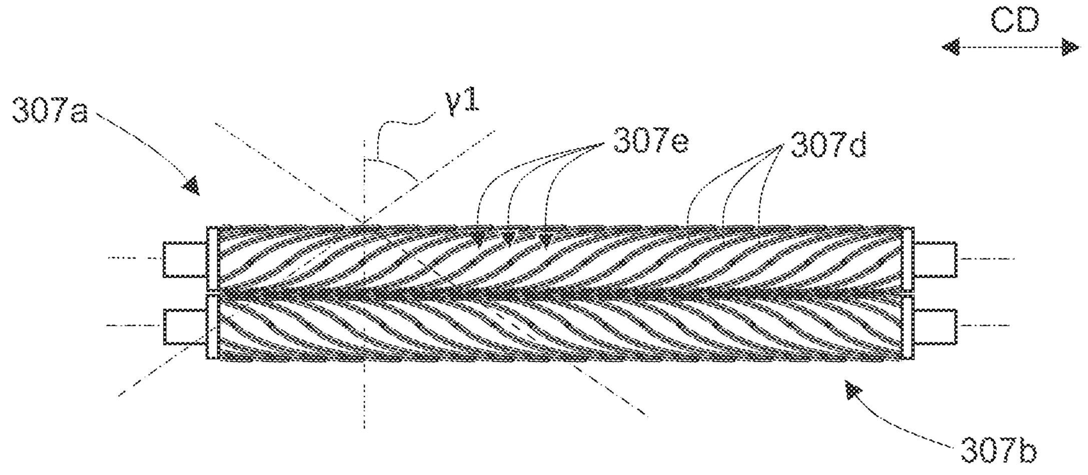
FIG. 16A is a view along the machine direction, of another example of a pair of deforming rollers.
Figure 16B:
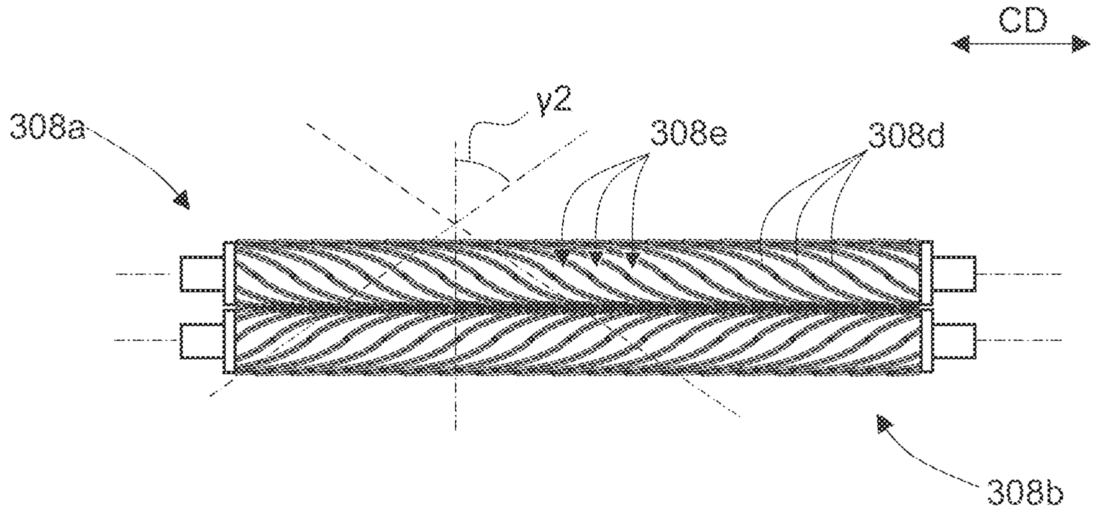
FIG. 16B is a view along the machine direction, of another example of a pair of deforming rollers.

Referring to FIG. 14, in another configuration, deforming rollers 306*a*, 306*b* may be configured with mating/engaging ridges 306*d* and grooves 306*e* about their circumferential surfaces, that are parallel with their axes of rotation. In this configuration, the rollers resemble a pair of mating, elongate spur gears with their axes oriented in the cross direction CD. A web passing through the nip between these rollers will be stretched over the respective "gear teeth", i.e., ridges 306*d*, substantially along a machine direction, rather than along a cross direction as described above and depicted in FIGS. 11 and 12.

Figure 8:
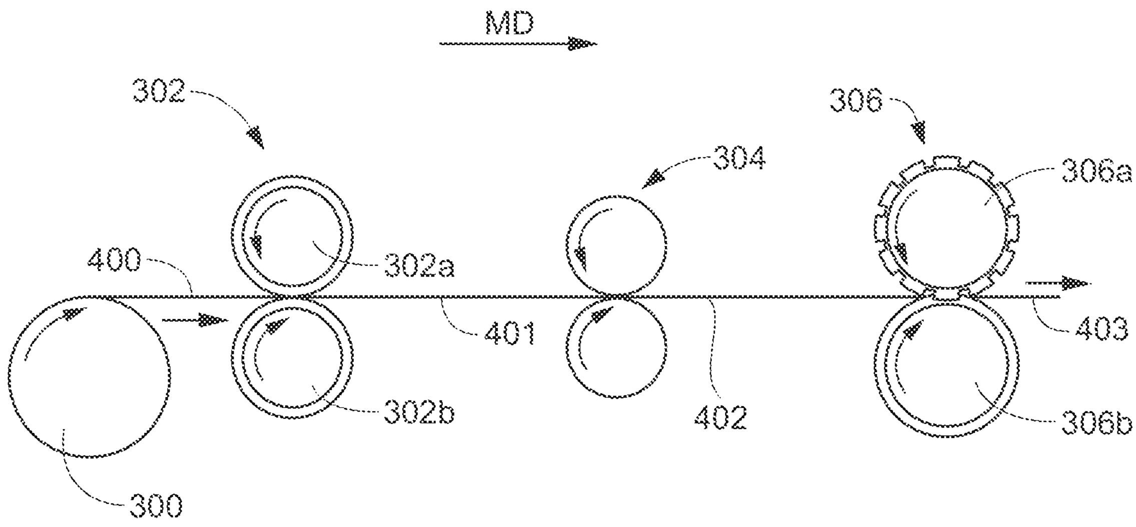
FIG. 8 is a simplified schematic side-view depiction of components arranged for a process for deforming a composite web.
Figure 9:
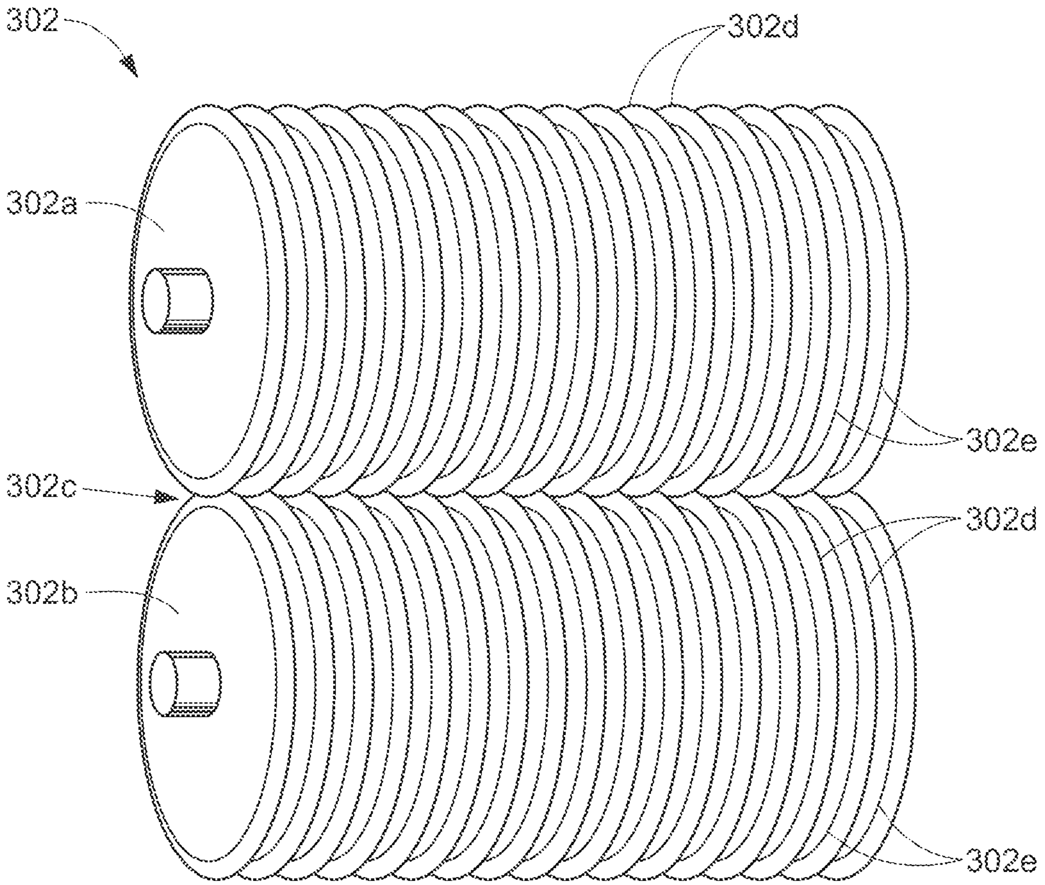
FIG. 9 is a perspective view of an example of a pair of deforming rollers.

Referring now to FIG. 8, it has been learned that a composite web 400 including an absorbent structure may be sequentially passed through the nips between two successive pairs of deforming rollers 302 and 306, causing the web to be incrementally stretched and/or fractured as described above, along two differing directions (in this particular non-limiting example, the machine direction and the cross direction). It has been learned that, following such deformation, compared with a similar structure that has not been so deformed, the absorbent structure (1) is dramatically faster at acquiring and distributing fluid therealong and therethrough; (2) exhibits comparatively greater absorption capacity per unit weight of absorbent material included, over the same time period; and (3) is dramatically more flexible and pliable, making it more capable of bending around and conforming to a non-ruled surface (i.e., body contours) and shifting with wearer body movement (i.e., moving and shifting along with underwear fabric, with wearer body movement). Without intending to be bound by theory, it is believed that an absorbent article having one or more layer components so processed will be dramatically more comfortable to a wearer/user of the product, and more effective at intercepting discharges of body fluids, as a result of greater conformability to body features and more rapid acceptance, distribution and absorption of fluid within its structure.

In the deformation process, the overall x-y plane surface area of the absorbent structure may be increased by up to about 35 percent or more. At the same time, the increase fluid acquisition and distribution speed capability and absorption capacity imparted to the article may enable the manufacturer to reduce or forego inclusion of particular material quantities and/or material layers (such as, for example, a separate acquisition/distribution layer), thereby enabling material cost savings as well as enable the manufacturer to offer a thinner, more comfortable and more discrete absorbent article (e.g. feminine hygiene pad) that performs at parity with thicker competing/comparable products, while being thinner, more discrete and more comfortable for the user. Because the pad is stretched and permanently deformed in the longitudinal and lateral directions (along x-y planar directions), the manufacturer may be able to reduce the overall x-y planar size of the absorbent structure and of the overall pad prior to deformation, and through the deformation process, cause the reduced-size pad structure to assume an expanded, final desired pad product size. The enhanced fluid acquisition speed and absorption capacity made possible via the deformation process makes more efficient use of the absorbent materials, and consequentially, a comparatively lesser quantity of absorbent material per pad is required to provide the desired fluid acquisition and absorption performance. Additionally, the deformation process described herein may eliminate the need to include apertures 43 (e.g., as shown in FIG. 2) through the absorbent structure, as described above, simplifying the manufacturing process.

In some configurations, the basis weight of the absorbent structure 40 may be from about 130 gsm to about 200 gsm.

It is believed that the enhanced liquid acquisition/distribution and absorption capabilities are attributable to the creation of added and/or larger internal voids (from fracturing of materials) within the absorbent structure, along the lines of deformation. Further, when the composite web 400 passed between the deforming rollers includes not only an absorbent structure but also one or both of a topsheet and backsheet components of an absorbent article, all of the layers may be deformed to varying extents depending upon their deformability or plastic extensibility, and all of the layers together as a composite can thereby be imparted with expanded size in the x-y directions, increased bidirectional extensibility, flexibility, and pliability.

This deformation along two directions is referred to herein as "bidirectional" deformation. Importantly, the bidirectionally-deformed composite web has enhanced capability to bend around and more closely conform to non-ruled, curving-contour surfaces such as the surfaces of human body features. The extent of this conformability is reflected in measurements that may be taken using the Conformability Force Measurement Method described below. In some configurations, the absorbent article described herein may exhibit a Conformability Force of from about 140 N/m to about 1500 N/m, or from about 150 N/m to about 1000 N/m, or from about 225 N/m to about 800 N/m. In contrast, current feminine hygiene pads exhibit a Conformability Force of greater than 1600 N/m, with some even greater than 5100 N/m. Without being limited by theory, it is believed that products that exhibit a Conformability Force of from about 140 N/m to about 1500 N/m are highly flexible and can move with the panty during wear, which can result in a more comfortable and/or closer fit to the body.

Referring to FIGS. 1, 4A-4C, 5, 11 and 12, the materials of the respective topsheet 20 and backsheet 30 may be selected and/or manufactured and/or formulated for having properties, and the engaging features and engagement depths of the deforming rollers may be configured and adjusted such that, for example, the topsheet and/or backsheet only stretch elastically but not plastically, or alternatively plastically but not to fracture/failure/breakage, in deformed zones 410, as they pass through the respective nips between the deforming rollers. In combination, the material (s)/layer(s) of the absorbent structure 40 may be selected and/or manufactured and/or formulated for having properties such that they will be stretched plastically or even to breakage/fracture, in an orderly manner and pattern in regions 410, reflecting the patterns of ridges and grooves on the deforming rollers. Preferably, the topsheet and backsheet are selected and/or manufactured and/or formulated such that they will be plastically (or permanently)stretched/deformed in zones 20*s*, 30*s*, substantially corresponding with lines of deformation 50, but not fractured in the deforming process, while the absorbent structure material 40 is stretched to fracture to create gaps 40*s*, also substantially corresponding with lines of deformation 50. In such a configuration, the combination of materials to form the absorbent article, as a composite, can be imparted with bidirectional extensibility and substantially enhanced pliability and body conformability.

When the topsheet and backsheet are only plastically stretched to greater x-y dimensions but not fractured, and one or more of the absorbent structure component(s)/layer(s) are stretched to fracture so as to form discrete fractured pieces 40*p* thereof, gaps 40*s* between fractured edges of the pieces substantially along lines of deformation 50 open up, thereby providing and opening fluid pathways through the absorbent structure, and providing added surface area of absorbent material, which fluid may contact so as to be absorbed more rapidly, as compared with an absorbent layer component that has not been so fractured. A non-limiting example of an absorbent article in the form of a feminine hygiene pad having undergone such bidirectional deformation along the CD and MD is schematically depicted in FIG. 1. The longitudinal/y and lateral/x directions of the pad correspond with the CD and MD directions of deformation, along lines of deformation 50, and are arranged at or approximately at 90 degrees from each other. Another non-limiting example of an absorbent article in the form of a feminine hygiene pad having undergone such bidirectional deformation, along angles oblique to the CD and MD, is schematically depicted in FIG. 5.

Figure 5:
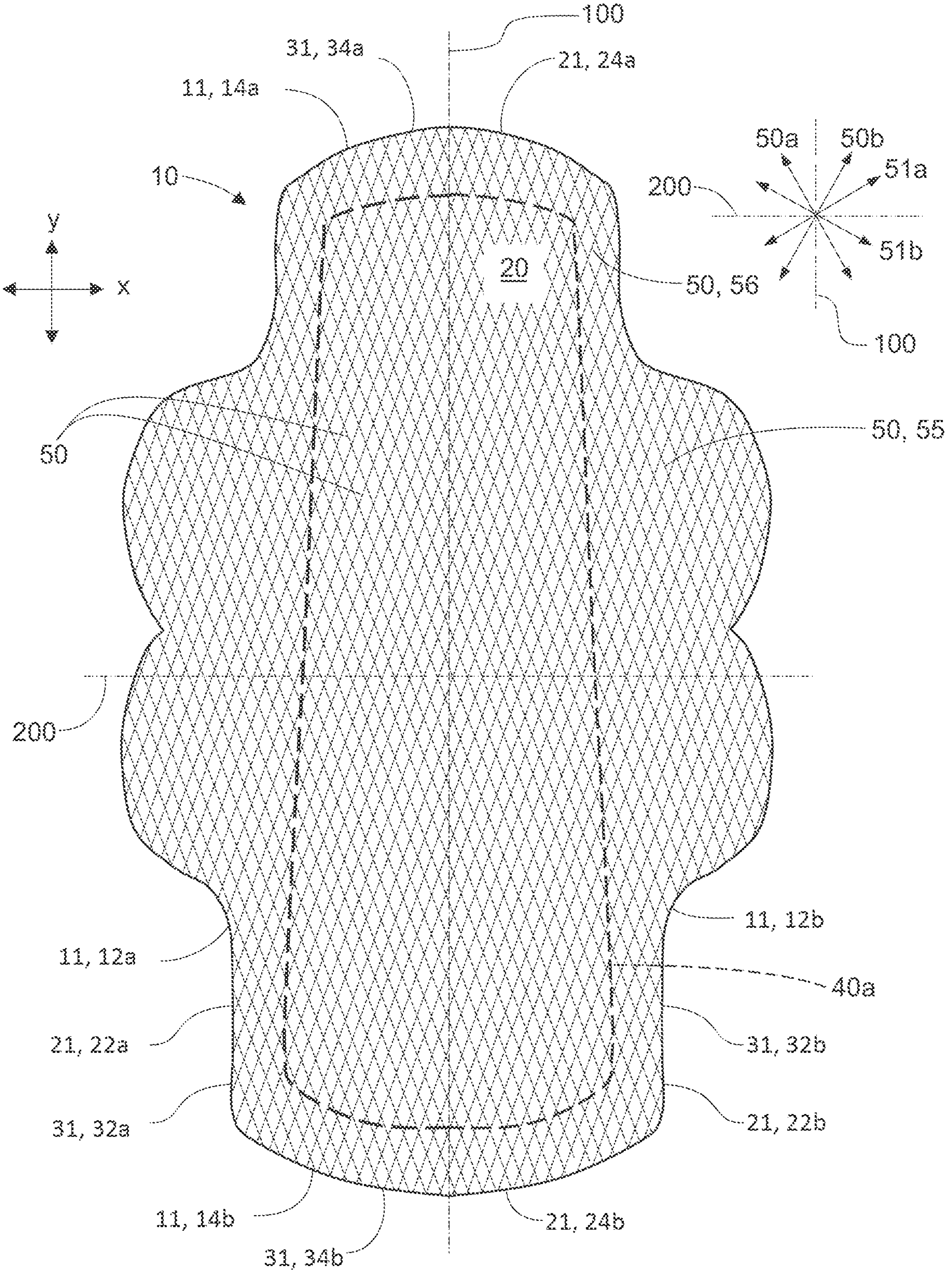
FIG. 5 is a plan view of another example of an absorbent article in the form of a feminine hygiene pad, wearer-facing side up, illustrating another example of a pattern of bidirectional deformation.

Referring to FIGS. 1 and 5, the absorbent article 10 comprises sides 11, for example a first side, a second side, a third side, and a fourth side. Absorbent article 10 may comprise a first longitudinal side 12*a* that extends in a direction substantially parallel to the longitudinal axis 100 and a second longitudinal side 12*b* opposite the first longitudinal side 12*a*. Absorbent article 10 may also comprise a first lateral side 14*a* that extends in a direction substantially parallel to the lateral axis 200 and a second lateral side 14*b* opposite the first lateral side 14*a*. As shown in FIG. 5, in some configurations, the absorbent article may comprise a first plurality of lines of deformation 55 extending in a first direction substantially perpendicular to a first stretch direction 51*a* and a second plurality of lines of deformation 56 extending in a second direction substantially perpendicular to a second stretch direction 51*b*. In some configurations, at least a portion of the first plurality of lines of deformation 55 extend from a first side of the absorbent article 10 to a second side of the absorbent article 10. In some configurations, a portion of the first plurality of lines of deformation 55 may extend from the first longitudinal side 12*a* to at least one of the second lateral side 14*b* and the second longitudinal side 12*b*. In some configurations, a portion of the second plurality of lines of deformation 56 may extend from the first longitudinal side 12*a* to at least one of the first lateral side 14*a* and the second longitudinal side 12*b*.

Referring to FIGS. 1, 4B-4D, and 5, the topsheet 20 and the backsheet 30 may comprise sides 21, 31, respectively. For example, topsheet 20 may comprise a first side, a second side, a third side, and a fourth side, and the backsheet 30 may comprise a first side, a second side, a third side, and a fourth side. The topsheet 20 may comprise a first longitudinal side 22*a* that extends in a direction substantially parallel to the longitudinal axis 100 and a second longitudinal side 22*b* opposite the first longitudinal side 22*a*. The topsheet 20 may also comprise a first lateral side 24*a* that extends in a direction substantially parallel to the lateral axis 200 and a second lateral side 24*b* opposite the first lateral side 24*a*. The backsheet 30 may comprise a first longitudinal side 32*a* that extends in a direction substantially parallel to the longitudinal axis 100 and a second longitudinal side 32*b* opposite the first longitudinal side 32*a*. The backsheet 30 may also comprise a first lateral side 34*a* that extends in a direction substantially parallel to the lateral axis 200 and a second lateral side 34*b* opposite the first lateral side 34*a*. In some configurations, the topsheet 20 and the backsheet 30 may each comprise plastically stretched zones 20*s*, 30*s* disposed substantially along the first plurality of lines of deformation 55 and the second plurality of lines of deformation 56. In some configurations, the topsheet 20 may comprise a plurality of plastically stretched zones 20*s* that extend continuously across the entire topsheet 20. In some configurations, a portion of the plastically stretched zones 20*s* of topsheet 20 may extend continuously from a first side of the topsheet 20 to a second side of the topsheet 20. For example, a portion of the plastically stretched zones 20*s* of topsheet 20 may extend continuously from the first longitudinal side 22*a* to the second longitudinal side 22*b*. In some configurations, a portion of the plastically stretched zones 20*s* of topsheet 20 may extend continuously from the first lateral side 24*a* to the second lateral side 24*b*. In some configurations, the backsheet 30 may comprise a plurality of plastically stretched zones 30*s* that extend continuously across the entire backsheet 30. In some configurations, a portion of the plastically stretched zones 30*s* of backsheet 30 may extend continuously from a first side of the backsheet 30 to a second side of the backsheet 30. For example, a portion of the plastically stretched zones 30*s* of backsheet 30 may extend continuously from the first longitudinal side 32*a* to the second longitudinal side 32*b*. In some configurations, a portion of the plastically stretched zones 30*s* of backsheet 30 may extend continuously from the first lateral side 34*a* to the second lateral side 34*b*.

For feminine hygiene pads having an absorbent foam layer (e.g., a HIPE foam layer as described above) forming part or substantially all of the absorbent structure 40, in order to provide the desired overall pad flexibility and effective fluid passageways, it may be desired that the deforming rollers be configured and dimensioned to impart plastic deformation to the topsheet and backsheet, together with fracture of the absorbent foam layer such that pieces 40*p* have an average x-y planar size, across the entirety of the absorbent structure, no greater than 15 mm, more preferably no greater than 10 mm, still more preferably no greater than 7 mm, and even more preferably no greater than 5 mm. (For purposes herein, the "x-y planar size" of a piece 40*p* is its greatest x-y planar dimension.) In some configurations, the average x-y planar size of the foam pieces 40*p* may be from about 1.5 mm to about 15 mm, or from about 2 mm to about 5 mm. In some configuration, the foam pieces 40*p* may have an x-y planar shape of a diamond. To achieve the enhanced fluid acquisition and absorbency performance and pad flexibility/pliability contemplated herein, it may be desired that the deforming rollers be configured and dimensioned to impart plastic deformation to the topsheet and backsheet, together with fracture of the absorbent foam layer, such that gaps 40*s* have an average x-y planar gap size, across the entirety of the absorbent structure, greater than 0.1 mm, more preferably 0.3 mm, still more preferably 0.6 mm, and even more preferably 1 mm, or from 0.3 mm to about 1.2 mm, or any sub-range therewithin. (For purposes herein, the "x-y planar gap size" of a gap 40*s* is the x-y planar dimension of the space between adjacent pieces, measured along a direction perpendicular to the corresponding line of deformation 50.) Alternatively, for the same purposes, it may be desired that the average x-y planar gap size be proportional to the average caliper ("C") of the absorbent structure 40. Thus, it may be desired that gaps 40*s* have an average x-y planar gap size, across the entirety of the absorbent structure, of at least (0.04×C), more preferably (0.12×C), still more preferably (0.24×C), and even more preferably (0.4×C), or from (0.04×C) to (0.48×C), or any sub-range therewithin.

Figure 4C:
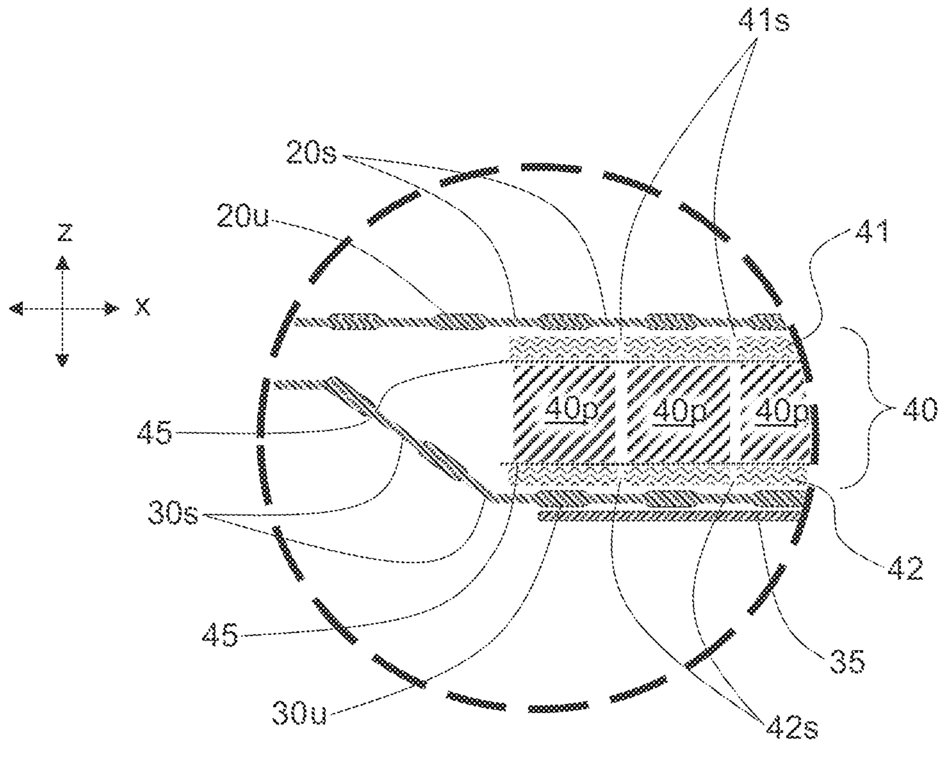
FIG. 4C is an enlarged view of the portion of FIG. 4A shown encircled in circle 4B, in FIG. 4A, in another possible example.
Figure 4D:
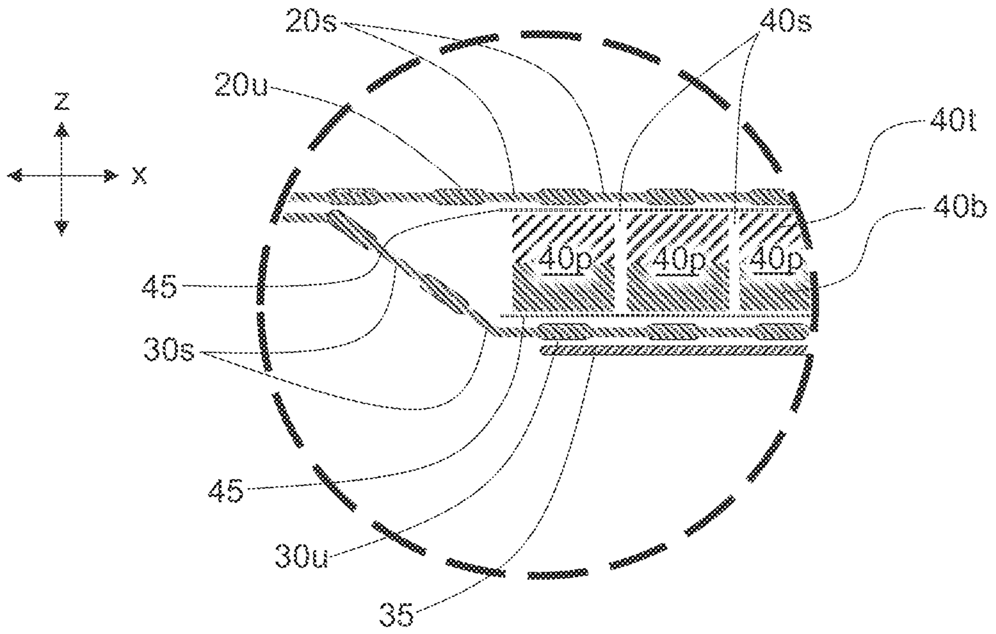
FIG. 4D is an enlarged view of the portion of FIG. 4A shown encircled in circle 4B, in FIG. 4A, in another possible example.

FIGS. 4A-4D schematically depict non-limiting examples of potential effects resulting from incremental stretching of a composite web including topsheet material, backsheet material and absorbent structure material, along the lateral direction of the pad depicted in FIG. 1. Topsheet may be imparted with plastically stretched zones 20*s*, and backsheet 30 may be imparted with plastically stretched zones 30*s*, in relatively orderly configurations along lines of deformation 50 (FIG. 1), along which plastic deformation of the topsheet material and/or backsheet material has occurred between roller teeth or ridges in the nip between the deforming rollers. Topsheet 20 and backsheet 30 may comprise zones of less or substantially no deformation 20*u*, 30*u*, respectively, disposed intermediate the plastically stretched zones. Absorbent structure 40 may be imparted with relatively orderly lines of plastic strain deformation or, preferably, fracture, to form gaps 40*s*. As depicted in FIG. 4C, in an alternative composite configuration, an absorbent structure 40 may include additional acquisition and/or distribution layers 41, 42, imparted with relatively orderly lines of strain deformation or even fracture to form strained regions or even gaps 41*s*, 42*s*. In some examples, additional layers 41, 42 may include nonwoven web materials, in which portions of an absorbent foam precursor have been integrated into the fibrous matrices thereof and subsequently cured or polymerized into foam structure, as suggested in, e.g., US2017/0119587; US2017/0119596; US2017/0119597; US2017/0119588; US2017/0119593; US2017/0119594; US2017/0119595; and US2017/0199598.

Figure 21A:
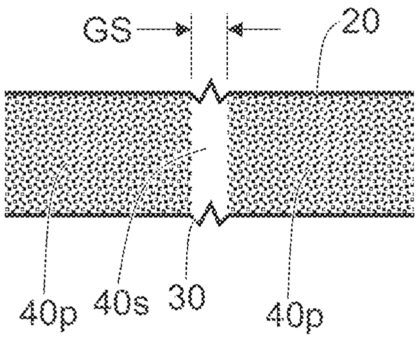
FIG. 21A is a magnified schematic cross section, along a plane along a z-direction, of a portion of an absorbent article including two adjacent pieces of an absorbent structure, shown in a flat configuration.
Figure 21B:
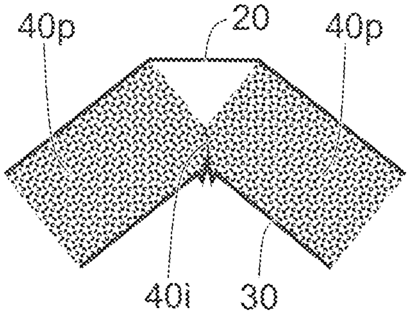
FIG. 21B is a magnified schematic cross section, along a plane along a z-direction, of a portion of an absorbent article including two adjacent pieces of an absorbent structure, shown in a bent configuration.
Figure 22A:
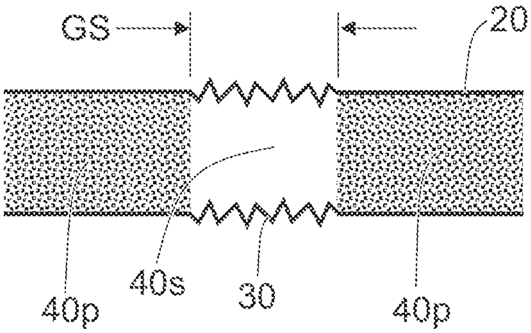
FIG. 22A is a magnified schematic cross section, along a plane along a z-direction, of a portion of an absorbent article including two adjacent pieces of an absorbent structure, shown in a flat configuration.
Figure 22B:
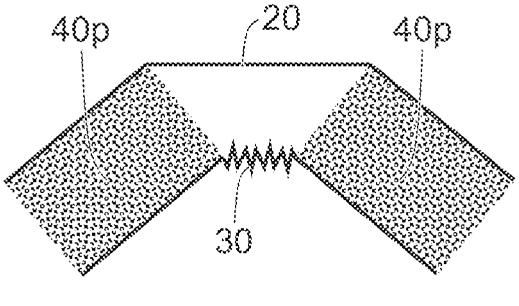
FIG. 22B is a magnified schematic cross section, along a plane along a z-direction, of a portion of an absorbent article including two adjacent pieces of an absorbent structure, shown in a bent configuration.

The size of the gaps 40*s* between foam pieces 40*p* in an article in which an absorbent foam as described herein forms or is a component of absorbent structure 40 may be adjusted via configuration of the deforming rollers. One aspect of such configuration that is particularly effective is the engagement depth ED of the respective, cooperating/meshing deforming ridges 302*d* and grooves 302*e* (see FIG. 10). Greater engagement depth ED will cause greater deformation of the topsheet and backsheet and thereby effect relatively larger gaps 40*s*, while lesser engagement depth ED will cause lesser deformation of the topsheet and backsheet and thereby effect relatively smaller gaps 40*s*. Generally, an article having gaps 40*s* large enough to allow bending thereacross with minimal interference between pieces 40*p* will be relatively more pliable and body-conformable, while an article having smaller gaps 40*s* that are not sufficient to allow bending thereacross without interference between pieces 40*p* will be relatively less pliable and body-conform-able. This effect of gap size GS is schematically illustrated in FIGS. 21A, 21B, 22A and 22B. FIG. 21A schematically illustrates the effect of deformation at a relatively lesser deforming roller engagement depth—relatively lesser deformation of topsheet 20 and backsheet 30, resulting in relatively smaller size GS of gaps 40*s* between pieces 40*p*. As a consequence, upon bending of the article in a z-direction, as one of the topsheet 20 and backsheet 30 are pulled taut, adjacent pieces 40*p* begin to interfere at interference location 40*i*. The cumulative effect of such interference between many pieces 40*p* at many gaps 40*s* within the article, impairs bending along the lines of deformation 50 and thereby reduces pliability and body-conformity of the article as a whole. Conversely, FIG. 22A illustrates the effect of deformation at a relatively greater deforming roller engagement depth—relatively greater deformation of topsheet 20 and backsheet 30, resulting in relatively greater size GS of gaps 40*s* between pieces 40*p*. As a consequence, upon bending of the article in a z-direction, pieces 40*p* are less likely to interfere upon bending. The cumulative effect of reduction of such interference between many pieces 40*p* within the article, eases bending along the lines of deformation 50 and thereby increases pliability and body-conformity of the article. Deforming roller engagement depth must be limited, however, so that topsheet 20 and backsheet 30 are not stretched to failure along lines of deformation 50, and/or so that potentially negative consumer perceptions of quality of the article (e.g., that the article is too flimsy or insubstantial, or damaged) do not arise.

Referring now to FIG. 5, in some examples, the absorbent article may be imparted with lines of deformation 50 that are oblique to the lateral axis 200 and longitudinal axis 100. To effect this result, in some examples, the combination web or an assembled article may be passed between machine-direction ring rollers 302*a*, 302*b* like those shown in FIGS. 9-11 and 13, by being fed therethrough in two successive steps, along two differing, oblique directional orientations relative the machine direction. In other examples (not illustrated), the combination web or assembled article progressing along a machine direction may be successively, intermittently immobilized and compressed or stamped along a z-direction, between pairs of flat deforming plates, which bear ridges and grooves suitably configured to incrementally stretch the web or article along oblique directions. However, for purposes of incrementally stretching a combination web along two differing directions oblique to a machine direction of continuous manufacturing, such methods may be found to be cumbersome and inefficient, as compared with using helical deforming rollers as described herein.

Figure 6:
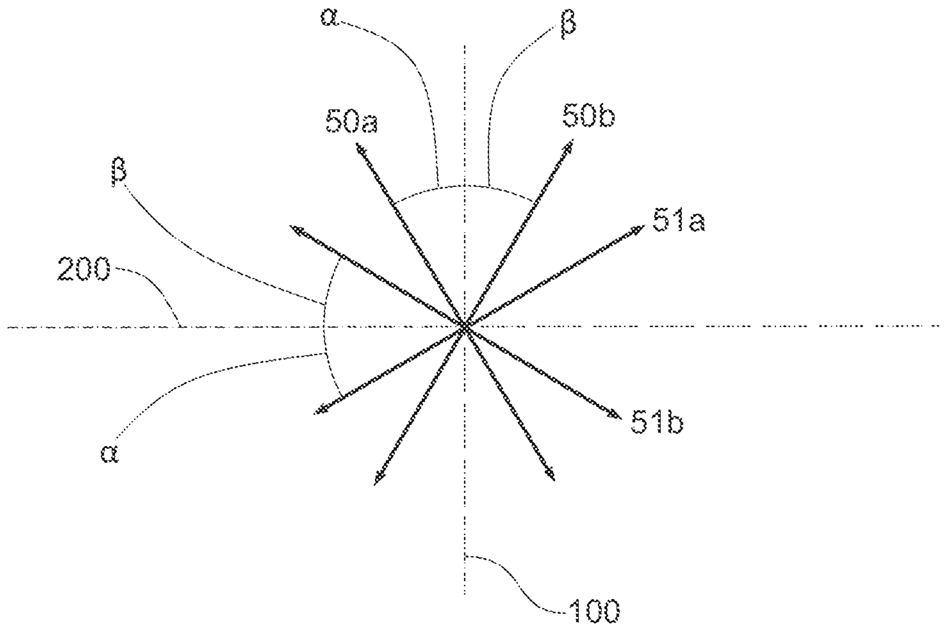
FIG. 6 is an enlarged view of arrows indicating directions of lines of stretch and of deformation along an x-y plane, relative longitudinal and lateral axes of an absorbent structure.

Alternatively, the deforming rollers used may be imparted with configurations resembling those of a mating/meshing pair of helical gears, spiral gears or worm gears (collectively herein, deforming rollers having a “helical” configuration of alternating grooves and ridges), as suggested in FIGS. 15A, 15B, 16A and 16B. As reflected in FIGS. 15A, 15B, 16A and 16B (and also referring to FIGS. 5 and 6), a first pair of such helical deforming rollers 307*a*, 307*b* may be configured to mesh and have helix angles $\gamma 1$ selected, upon passage of an article (or precursor combination web) through a nip therebetween, to impart the article 10 with lines of deformation 50 substantially parallel with one of line of deformation directions 50*a*, 50*b*, by incrementally straining the article along one of strain directions 51*a*, 51*b*. Following passage through the nip between rollers 307*a*, 307*b*, the article (or precursor combination web) may be passed through a second nip between a second pair of deforming rollers 308*a*, 308*b* (FIGS. 15B, 16B), which also may be configured to be helical and be adapted to mesh and be configured with helix angles $\gamma 2$ selected, upon passage of the article (or precursor combination web) through the nip therebetween, to impart the article 10 with lines of deformation 50 substantially parallel with the other of line of deformation directions 50*a*, 50*b*, by incrementally straining the article along the other of strain directions 51*a*, 51*b*.

With such a configuration, the resulting deformation of the web passing through a nip therebetween will occur along lines of deformation 50 that are oblique relative the MD and CD on the web, with respect to the machine and cross directions, along an angle of deformation imparted as a result of the helix angles of the helical ridges 307*d*, 308*d* and meshing helical grooves 307*e*, 308*e* along the outer circumferences or outer radial edges of the rollers. Two successive pairs of such helical deforming rollers having differing or oppositely-oriented helix angles may be arranged along a processing line to successively strain and deform a composite web along two differing directions and thus impart bidirectional deformation to the article or a precursor web thereof, for example, as suggested in FIG. 5. It may be preferred that the helix angles of the successive helical deforming roller pairs be selected such that the angles $\alpha$ and $\beta$ formed at the intersection of resulting lines of deformation 50 with the longitudinal axis of the article, be substantially equal, for purposes of imparting stretch/elongation/conformability characteristics to the article, and appearance, that is substantially symmetrical about and/or aligned with the longitudinal axis.

Referring back to FIGS. 5 and 6, helical deforming rollers may be configured to impart bidirectional strain and deformation along strain directions 51*a*, 51*b* that are oblique with respect to the longitudinal/x and lateral/y directions of an absorbent article 10 such as a feminine hygiene pad. For a feminine hygiene pad, it has been learned that a bidirectionally deformed pad with lines of deformation 50 parallel to line of deformation directions 50*a*, 50*b*, which are substantially perpendicular to strain directions 51*a*, 51*b*, which strain directions are oriented at angles $\alpha$ and $\beta$ with respect to the lateral direction, respectively, more readily shifts and accommodates a wearer’s body (e.g., walking) movements well, when adhered to the inside of the wearer’s underwear in the crotch region thereof, when angles $\alpha$ and $\beta$ are each about 5 degrees to about 85 degrees, more preferably about 15 degrees to about 70 degrees, and even more preferably about 30 degrees to about 60 degrees. Correspondingly, it is preferred that line of deformation directions 50*a*, 50*b* each be about 5 degrees to about 85 degrees, more preferably about 15 degrees to about 70 degrees, and even more preferably about 30 degrees to about 60 degrees, with respect to the longitudinal axis of the article. All subranges within these ranges are contemplated herein.

Adhered to the inside surface of the wearer’s underwear, the pad is better able to shift and move along with the fabric of the underwear as the wearer moves about. This results in a dramatic improvement to wearer comfort.

It has also been learned that such strain directions, being oblique with respect to the machine direction of movement of the web through the nip, are less likely to be destructive of a nonwoven web material, than a strain along a direction that is parallel or perpendicular to the machine direction (as would be imparted by rollers such as those shown in FIGS. 9-14). This is believed to be a previously unrecognized synergistic benefit, resulting from the typical machine direction bias of fibers in nonwoven web materials, particularly spunbond nonwoven web materials. Spunbond nonwoven web materials typically have a machine direction bias as a result of the manner in which they are manufactured, i.e., by deposition of spun fibers upon a forming belt moving along a machine direction. (Herein, "machine direction bias," with respect to the fibers forming a nonwoven web, means that a majority of the fibers, as situated in the web and unstretched, have lengths with machine direction vector components that are greater than their cross direction vector components.) As a result of the manner in which articles 10 and their component web materials are typically manufactured, the nonwoven web components typically have a machine direction bias that coincides with the longitudinal (y) direction of the article. When the deformation directions 51*a*, 51*b* are oblique with respect to the machine/longitudinal directions as suggested in FIGS. 5 and 6, fibers are less likely to be pulled directly along their lengths in the machine direction or separated in the cross direction, and as a result, are less likely to be stretched along their lengths beyond their limits and break, and less likely to be separated along a cross direction, which can result in unwanted change or damage to the structural integrity and quality of the web material.

It is contemplated that a pair of deforming rollers may be configured to impart bidirectional deformation to a composite web in a single pass through the nip, i.e., wherein features of the rollers are configured to cause incremental stretching of the composite web simultaneously in two differing directions, including directions parallel and orthogonal to the machine direction, or oblique to the machine direction, as described above. It may be preferred, however, to impart stretching along two differing directions, successively, via two successive pairs of deforming rollers. This may enable better control over the stretching process along each direction, and reduce chances of undesired lines or paths of fracture in the absorbent structure, or damage to components of the web.

It is also contemplated that one or more pairs of deforming rollers may be configured to deform only discrete regions or zones of a composite web, while leaving adjacent regions or zones undeformed. By way of non-limiting example depicted in FIG. 7, an article in the form of a feminine hygiene pad 10 may be bidirectionally deformed only in a defined zone or region (in the non-limiting example shown in FIG. 7, the center region shown with oblique lines of deformation 50), while the remaining areas are left undeformed. The bidirectional deformation may be imparted along directions 50*a*, 50*b* and 51*a*, 51*b* angles $\alpha$ and $\beta$, as described above. In the examples shown in FIG. 7, a center region is deformed, and side regions including wings 15 are left undeformed. Regions of deformation and regions to be left undeformed may be configured for various effects.

Figure 7:
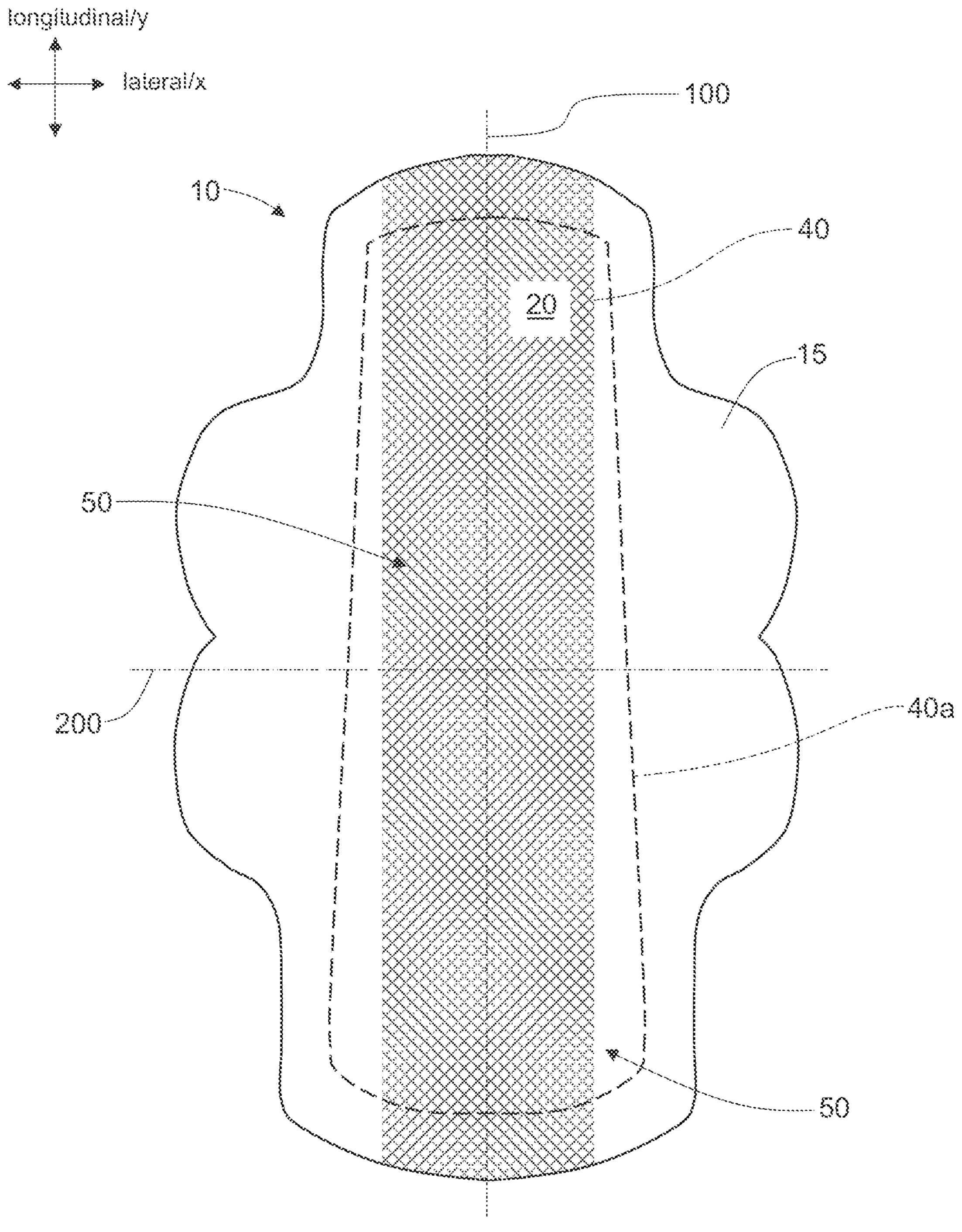
FIG. 7 is a plan view of another example of an absorbent article in the form of a feminine hygiene pad, wearer-facing side up, illustrating particular features.

It may be preferred, however, to bidirectionally deform the entirety of the x-y area of the layered materials forming the article 10 (as suggested in FIGS. 1 and 5), with no breaks or discontinuities in the bidirectional deformation pattern like, for example, that shown in FIG. 7, wherein a portion or portions have been left undeformed. This is because a discontinuity or interruption in the bidirectional deformation pattern can result in discontinuity of the pliability and flexibility imparted by the deformations, compromising the ability of the article 10 to closely conform to a wearer's body features and shift with the fabric of the wearer's underwear and/or the wearer's body movements.

Figure 19:
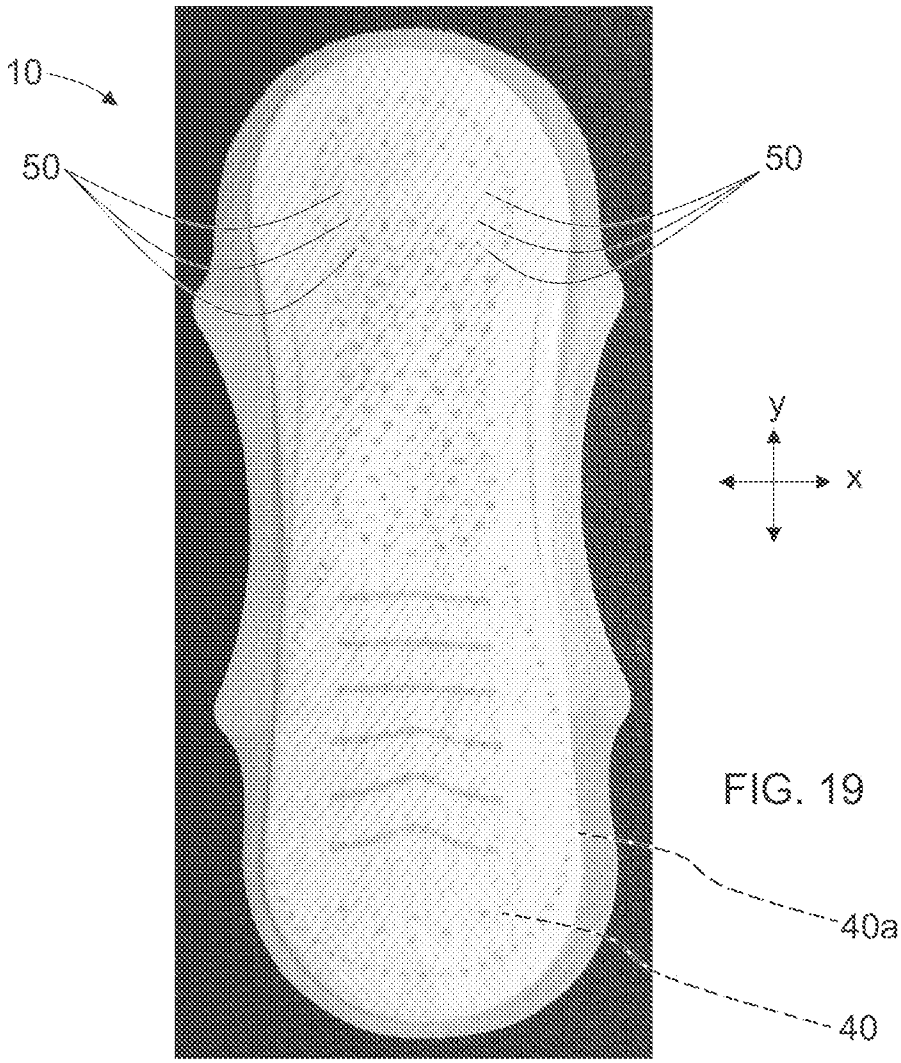
FIG. 19 is a reproduction of a photograph of an absorbent article in the form of a feminine hygiene pad, wearer-facing side up, imparted with an example of a pattern of bidirectional deformation.
Figure 20:
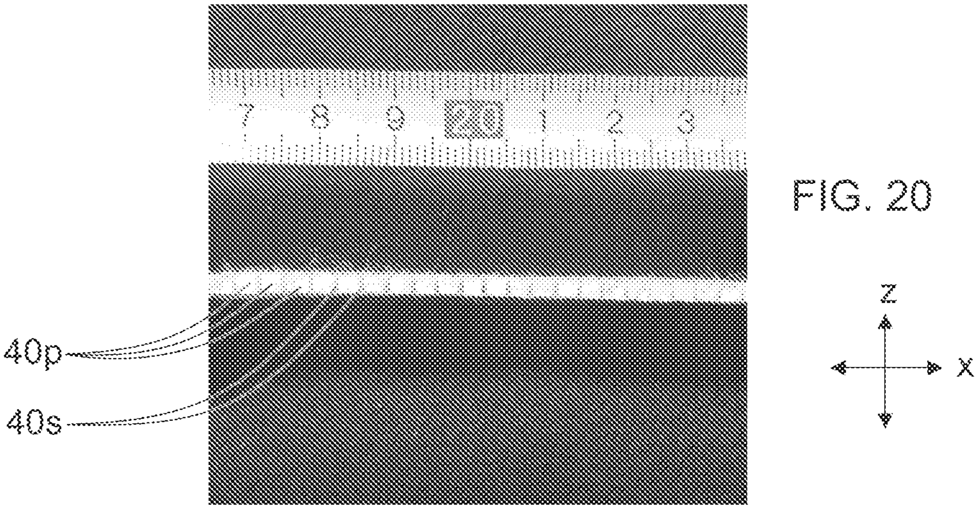
FIG. 20 is a reproduction of a portion of a photograph of a lateral cross section cut of the absorbent article shown in FIG. 19, shown adjacent to a ruler bearing centimeter/millimeter demarcations.

Referring again to FIGS. 1, 4A-4D, 19 and 20, as discussed above, the bidirectional deformation process may be configured to fracture material of the absorbent structure 40 along lines of deformation 50 in an orderly manner, into a plurality of discrete pieces 40*p*. Where, for example, the material of structure 40 includes a layer of material that is relatively inelastic or brittle in tension (such as, for example, absorbent foam of suitable composition as described herein), the process, suitably configured, will fracture the structure 40 in an orderly manner to create roughly evenly-sized discrete pieces 40*p* separated by gaps 40*s*, divided along the lines of deformation 50. Photographs of an actual prototype example of an absorbent article 10 depicting such lines of deformation 50, pieces 40*p* and gaps 40*s* are reproduced in FIGS. 19 and 20.

In order to prevent the discrete pieces 40*p*, following fracture, from becoming dislodged and dislocated within the structure (i.e., to hold them in place substantially in their relative pre-fracture positions), it may be desirable to include structure to hold them in place, within the enveloped space between the topsheet and the backsheet. For this purpose, deposits 45 of a suitable adhesive/glue material may be disposed in locations between one or both of the wearer-facing and outward-facing interfaces between the absorbent structure 40 and the topsheet, and backsheet, respectively, or between the absorbent structure and other interlayered components such as, for example, distribution layer(s). Particularly for adhesive that may be disposed between the wearer-facing surface of the absorbent structure 40 and the topsheet 20, the deposits 45 may be applied via controlled spraying in the manner discussed above, so as not to create an occlusive film of adhesive, but to bond the respective materials together at discrete locations corresponding to deposited glue droplets, while avoiding creation of a fluid barrier, and leaving the absorbent structure 40 effectively unoccluded on its wearer-facing surface. In some configurations, however, it may be deemed suitable or even preferred that an application of adhesive disposed between the outward-facing surface of the absorbent structure 40 and the backsheet be more extensive, continuous or even substantially film-like, since occlusion at or on the outward-facing surface of the absorbent structure (e.g., a layer of absorbent foam) may be of less concern; and such more extensive or continuous application may better serve to hold fractured pieces 40*p* of absorbent structure 40 in place, following deformation as described herein. Thus, the adhesive deposits may be disposed at both the upper and lower surfaces of the absorbent structure 40 or a layer component thereof to provide a more cohesive overall pad structure and minimize chances that pieces 40*p* can be dislodged and dislocated within the structure.

Preferably, the adhesive deposits are applied across a majority of the x-y plane surface area of one or both of the wearer-facing surface and the garment-facing surfaces of the absorbent structure 40. To reduce chances of a stiffening effect resulting from application of the adhesive/glue between respective subjacent/superadjacent layers of the pad, it may be desired that the adhesive/glue material selected be of an elastic and/or resilient formulation. In some configurations, the adhesive may be a pressure sensitive adhesive with a relatively long open time. Suitable adhesives may have a relatively high elastic modulus (G') to withstand the forces applied during mechanical processing as the materials are stretched. Adhesives utilizing a styrene/isoprene/styrene (SIS) building block may be preferred. One suitable example may be an adhesive of the designation H2031-C5X, a product of Bostik, a division or subsidiary of the Arkema Group, Columbes, France.

In some configurations, adhesive may be disposed between the wearer-facing surface of the absorbent structure 40 and the topsheet as shown and described in FIGS. 3A-3D. In some configurations, adhesive may be disposed between the wearer-facing surface of the absorbent structure 40 and the topsheet at a basis weight of from about 15 gsm to about 35 gsm, or from about 18 gsm to about 32 gsm, or from about 20 gsm to about 30 gsm, specifically reciting all values within these ranges and any ranges created thereby. In some configurations, adhesive may be disposed between the outward-facing surface of the absorbent structure 40 and the backsheet at a basis weight of from about 15 gsm to about 35 gsm, or from about 18 gsm to about 32 gsm, or from about 20 gsm to about 30 gsm, specifically reciting all values within these ranges and any ranges created thereby. Consumer testing has surprisingly revealed that when the basis weight of the adhesive between the topsheet and absorbent structure and/or between the backsheet and absorbent structure is below 15 gsm, respectively, the pieces of foam can become dislodged and dislocated within the absorbent article during wear, creating a non-uniform distribution of absorbent material which can negatively impact comfort and/or fluid handling performance.

It will be appreciated that the absorbent structure described above may be adapted not only for use as a feminine hygiene pad, but also an incontinence pad or absorbent insert for use within underwear, or even as a structural subcomponent of disposable menstrual underwear or disposable adult incontinence underwear adapted for use/wear by men or women.

In some configurations, an absorbent article structure manufactured as described herein may have a porous/liquid permeable nonwoven web material (such as a spunbond web material) substituted for either or both of the materials of the topsheet 20 and backsheet 30 as described above, similarly positioned and disposed, such that fluid may freely pass into and out of the structure at both of its upper and lower surfaces. The structure may be mechanically processed as described above, for similar effects and benefits as described above. Such an absorbent article structure may then be incorporated as a layer component of, for example, an absorbent core structure in an absorbent article such as, for example, a disposable infant/child diaper, a disposable child training pant, a disposable feminine hygiene pad, a disposable incontinence pad, disposable menstrual underwear or disposable incontinence underwear.

Test/Measurement Methods

Capillary Work Potential via Pore Volume Distribution

Pore Volume Distribution determines the estimated porosity of the effective pores within a porous sample by measuring the fluid movement into and out of said sample as stepped, controlled differential pressure is applied to the sample in a sample chamber. The incremental and cumulative quantity of fluid that is thereby absorbed/drained by the porous sample at each pressure is then determined. In turn, work done by the porous sample normalized by the area of said sample is calculated as Capillary Work Potential.

Method Principle

For uniform cylindrical pores, the radius of a pore is related to the differential pressure required to fill or empty the pore by the following equation:

$$\text{Differential Pressure}=[2\gamma \cos \Theta)]/r$$

where $\gamma$=liquid surface tension, $\Theta$=contact angle, and r=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure, characterize the effective pore radius distribution in said porous material. (Because nonuniform pores are approximated as uniform by the use of an effective pore radius, this general methodology may not produce results precisely in agreement with measurements of void dimensions obtained by other methods such as microscopy.)

The Pore Volume Distribution method uses the above principle and is reduced to practice using the apparatus and approach described in "Liquid Porosimetry: New Methodologies and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous sample as the differential air pressure is changed between ambient ("lab") air pressure and a slightly elevated air pressure (positive differential pressure) surrounding the sample in a sample test chamber. The sample is introduced to the sample chamber dry, and the sample chamber is controlled at a positive differential pressure (relative to the lab) sufficient to prevent fluid uptake into the sample after the fluid bridge is opened. After opening the fluid bridge, the differential air pressure is decreased in steps to 0, and in this process subpopulations of pores within the sample acquire liquid according to their effective pore radius. After reaching a minimal differential pressure at which the mass of fluid within the sample is at a maximum, differential pressure is increased stepwise again toward the starting pressure, and the liquid is drained from the sample. The absorption portion of the stepped sequence begins at the maximum differential pressure (smallest corresponding effective pore radius) and ends at the minimum differential pressure (largest corresponding effective pore radius). The drainage portion of the sequence begins at the minimum pressure differential and ends at the maximum pressure differential. After correcting for any fluid movement for each particular pressure step measured on the chamber while empty for the entire absorption/drainage sequence, the fluid uptake by the sample (mg) as well as cumulative volume ($mm^3$/mg) at each differential pressure is determined in this method.

Sample Conditioning and Sample Preparation

The Pore Volume Distribution method is conducted on samples that have been conditioned for at least 2 hours in a room maintained at a temperature of 23° C.±2.0° C. and a relative humidity of 50%±2%, and all tests are conducted under the same environmental conditions in such conditioned room. Any damaged product or sample that has defects such as wrinkles, tears, holes, and similar are not tested. A sample conditioned as described herein is considered dry for purposes of this invention. Determine which side of the sample is intended to face the wearer in use, then cut it to 55 mm long by 55 mm wide. Measure the mass of the sample and record to the nearest 0.1 mg. Three samples are measured for any given material being tested, and the results from those three replicates are averaged to give the final reported values.

Apparatus

Apparatus suitable for this method is described in "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mm $H_2O$ and 1098 mm $H_2O$ differential pressure may be used in place of the pressure-control subsystem described in this reference. One example of a suitable overall instrumentation and software is the TRI/Autoporosimeter (Textile Research Institute (TRI)/Princeton Inc. of Princeton, NJ, USA). The TRI/Autoporosimeter is an automated computer-controlled instrument for measuring pore volume distributions in porous materials (e.g. the volumes of different size pores within the range from 5 μm to 1200 μm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyze the measured data.

Figure 18:
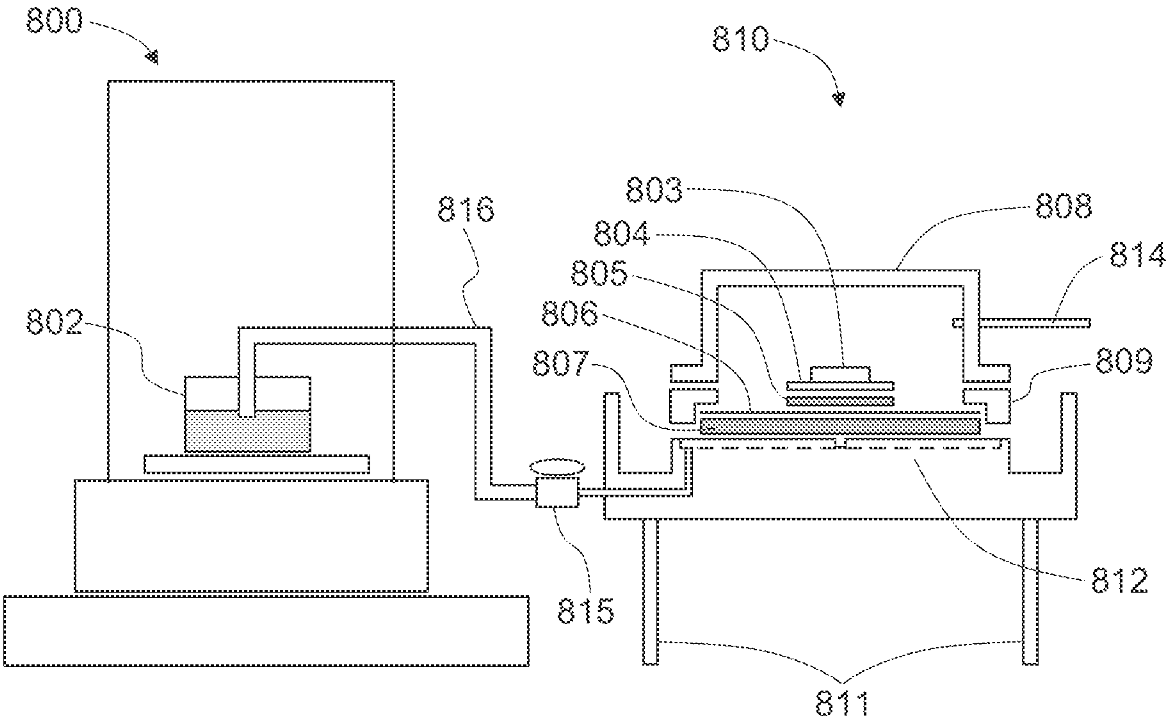
FIG. 18 is a schematic depiction of equipment used in the Capillary Work Potential via Pore Volume Distribution method, described herein.

A schematic depiction of suitable equipment is shown in FIG. 18. The equipment consists of a balance 800 with fluid reservoir 802 which is in direct fluid communication with the sample 805 which resides in a sealed, air-pressurized sample chamber 810. The fluid communication between the reservoir 802 and the sample chamber 810 is controlled by valve 815. A weight 803 placed on top of a Plexiglass plate 804 (55 mm long by 55 mm wide) is used to apply a confining pressure of 0.25 psi on the test sample to ensure good contact between the sample and a fluid saturated membrane 806 throughout the test. The membrane 806 (90 mm diameter, 150 um thick, 1.2 μm pore size; mixed cellulose ester filter RAWP09024; available from Millipore Corporation of Bedford, MA) is attached to a macro-porous frit 807 (Monet plate with 90 mm diameter, 60 mm thick; available from Mott Corporation, Farmington, CT, or equivalent) as follows. Adhere the membrane 806 to the frit 807 using Krylon® spray paint (Gloss White Spray Paint #1501; available from FilmTools, or equivalent) as the adhesive. Allow the prepared membrane/frit assembly to dry prior to use.

To prepare the equipment for testing, fill the inner base 812 of the sample chamber 810 with test fluid. The test fluid is degassed 0.9% saline solution, prepared by adding 9.0 g of reagent grade NaCl per 1 L of deionized water (liquid density is 1.01 g/cm$^3$, surface tension $\gamma$ to be 72.3±1 mN/m, contact angle cos $\Theta$=0.37). Place the membrane/frit assembly, membrane 806 side up, onto the inner base 812 of the sample chamber 810, and secure it into place with a locking collar 809. Fill the reservoir 802 and connecting tube 816 with test fluid. Open valve 815 and ensure that no air bubbles are trapped within the connecting tube or the pores within the membrane/frit assembly. Using the legs 811 of the sample chamber 810, level the sample chamber and adjust the height of the sample chamber (and/or the amount of fluid in the reservoir 802) as necessary, to bring the top surface of the membrane 806 into the same horizontal plane as the top surface of the fluid in the reservoir 802.

Program the system to progress through a sequence of stepped differential pressures (in mm $H_2O$) as follows: 1098, 549, 366, 275, 220, 183, 137, 110, 92, 78, 69, 61, 55, 50, 46, 42, 39, 37, 34, 32, 31, 29, 27, 24, 22, 20, 18, 14, 9.2, 6.9, 5.5, 4.6, 5.5, 6.9, 9.2, 14, 18, 20, 22, 24, 27, 29, 31, 32, 34, 37, 39, 42, 46, 50, 55, 61, 69, 78, 92, 110, 137, 183, 220, 275, 366, 549, 1098. These pressures correlate to effective pore radii from 5 μm (1098 mm $H_2O$) to 1200 μm (4.6 mm $H_2O$). The criterion for moving from one pressure step to the next is that fluid uptake/drainage to/from the sample, measured at the balance 800, is less than 10 mg/min for 15 seconds.

Method Procedure

Check the system for leaks and ensure the maximum test pressure can be reached as follows. With liquid valve 815 open, place the top 808 of the sample chamber 810 in place and seal the chamber. Apply sufficient air pressure to the chamber 810 (via connection 814) to achieve a differential pressure of 1098 mm $H_2O$ (5 μm effective pore radius). Close the liquid valve 815 then open the sample chamber. Place the sample 805 (wearer side facing down) directly onto the membrane 806, then place the cover plate 804 and confining weight 803 centered over the sample. Replace the top 808 and reseal the sample chamber 810. Open the liquid valve 815 to allow movement of fluid between the liquid reservoir 802 and the sample and start the test to progress through the pre-specified sequence of differential pressures. The amount of fluid absorbed (or drained) by the sample at each pressure step over the entire sequence is recorded as Uptake to the nearest 0.1 mg.

A separate "blank" measurement is performed by following this same method procedure (same stepped sequence of differential pressures) on an empty sample chamber with no sample 805, cover plate 804 or confining weight 803 present on the membrane/frit assembly. Any fluid movement observed is recorded (mg) at each of the pressure steps. Fluid uptake data for the sample are corrected for any fluid movement associated with the empty sample chamber by subtracting fluid uptake values of this "blank" measurement from corresponding values in the measurement of the sample, and recorded as Blank Corrected Sample Uptake to the nearest 0.1 mg.

Determination of Capillary Pressure, Cumulative Volume and Capillary Work Potential The % Saturation of the sample at each of the pressure steps for both the absorption and drainage portions of the test sequence can be calculated by dividing the maximum Blank Corrected Sample Uptake (mg) by the Blank Corrected Sample Uptake (mg), then multiplying by 100. From the data collected across the entire sequence, one of average skill in the art can then determine the % Saturation at any given capillary absorption pressure (CAP) or capillary desorption (drainage) pressure (CDP). The CAP and CDP are reported to the nearest 0.1 mm $H_2O$ for any specified % Saturation.

The cumulative volume is calculated for each of the pressure steps by the following equation:

Cumulative Volume (mm$^3$/mg)=Blank Corrected Sample Uptake (mg)/Fluid Density (g/cm$^3$)/Mass of Sample (mg)

The Capillary Work Potential (CWP) is the work done by the sample normalized by the area of the sample. The trapezoidal rule is used to integrate the ith Pressure as a function of Cumulative Volume over n data points for the absorption and drainage portions of the cycle.

$$CWP\left[\frac{mJ}{m^2}\right] = \frac{W}{A_w} = \sum_{i=1}^{n} \frac{1}{2} \frac{m_w(CV_{i+1} - CV_i)(P_i + P_{i+1})}{A_w} \left(10^3\left[\frac{mJ}{J}\right]\right)$$

where $m_w$=mass of sample (mg)

CV=Cumulative Volume (m$^3$/mg)

P=Air Pressure (Pa)

$A_w$=Area of sample on one side (m$^2$)

Report the CWP, CWPA and CWPD to the nearest 0.1 mJ/m$^2$, where CWPA represents the absorption portion of the pressure sequence and CWPD represents the drainage portion of the pressure sequence.

Caliper Measurement

The caliper, or thickness, of a test sample of a nonwoven web, laminate, foam layer material, or combination thereof, is measured as the distance between a reference platform on which the sample rests and a pressure foot that exerts a specified amount of pressure onto the sample over a specified amount of time. All measurements are performed in a laboratory maintained at 23° C.±2 C.° and 50%±2% relative humidity and test samples are conditioned in this environment for at least 2 hours prior to testing.

Caliper is measured with a manually-operated micrometer equipped with a pressure foot capable of exerting a steady pressure of 2.0 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test sample and capable of exerting the required pressure. A suitable pressure foot has a diameter of 25.4 mm, however a smaller or larger foot can be used depending on the size of the sample being measured. The test sample is supported by a horizontal flat reference platform that is larger than and parallel to the surface of the pressure foot. The system is calibrated and operated per the manufacturer's instructions.

Obtain a test sample, if necessary by removing it from an absorbent article. When excising the test sample from an absorbent article, use care to not impart any contamination or dimensional deformation to the test sample. The test sample is obtained from an area free of folds or wrinkles, and it must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm±1.0 mm per second until the full pressure is exerted onto the test sample. Wait 5 seconds and then record the caliper of the test sample to the nearest 0.01 mm. In like fashion, repeat for a total of five replicate test samples. Calculate the arithmetic mean for all caliper measurements and report as Caliper to the nearest 0.01 mm.

Conformability Force Measurement Method

Measurements made using this Conformability Force Measurement Method reflect the extent to which a composite web material (i.e., combination, assembly or laminate of web materials) will resist bending and stretching around a non-ruled surface. A composite web material that is bidirectionally extensible will more readily bend and stretch around a non-ruled surface, than a comparable composite that is not bidirectionally extensible. In this method, the non-ruled surface is a spherical ball that is 25.4 mm in diameter.

The Conformability Force Measurement Method is performed on a constant rate of extension tensile tester (a suitable instrument is MTS Insight tensile tester operated under TestSuite software, MTS Systems Corp, Eden Prairie, MN, or equivalent) using custom fixtures and an appropriate capacity load cell. All testing is performed in a laboratory controlled at 23° C.±2 C. ° and 50%±2% relative humidity.

Figure 17:
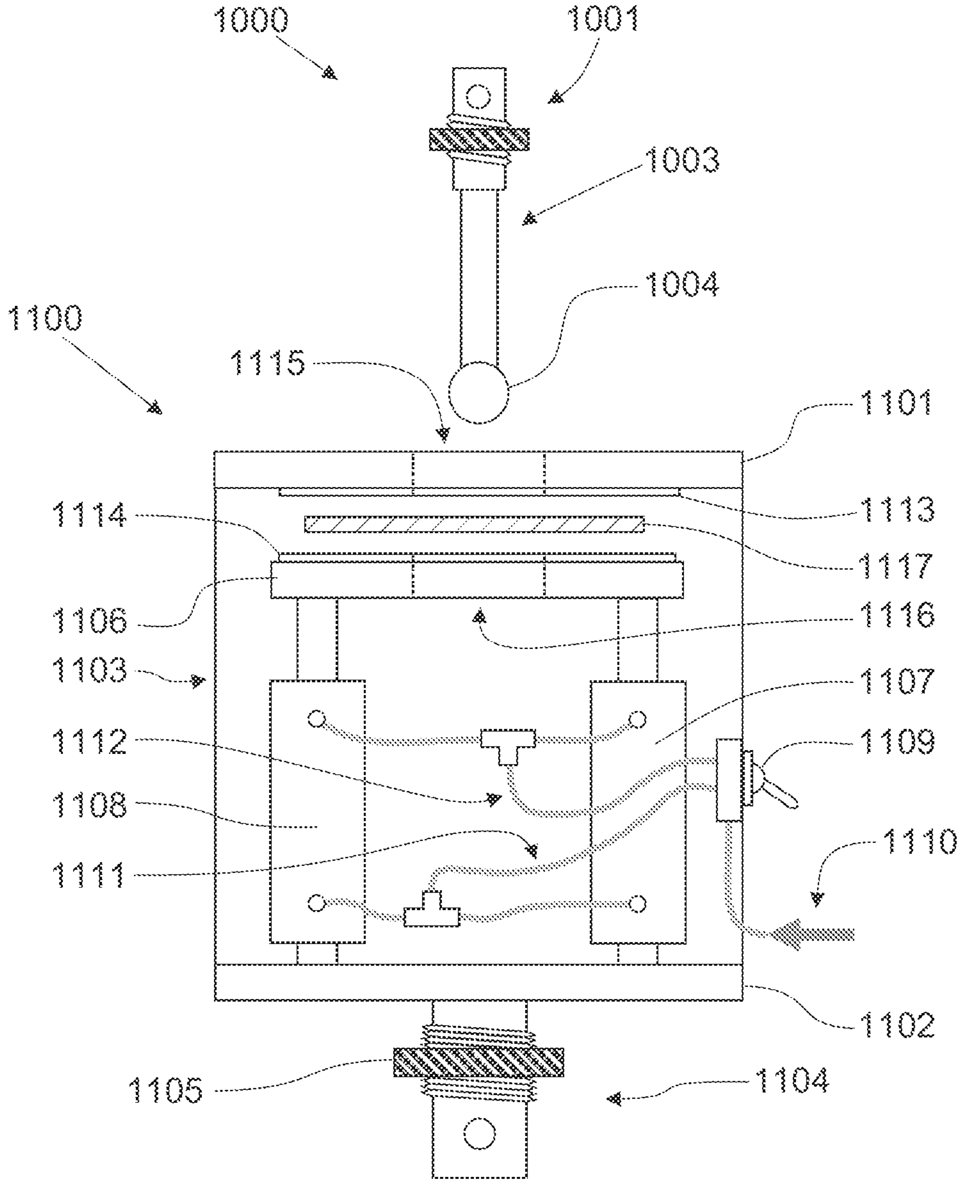
FIG. 17 is a schematic depiction of equipment used in the Conformability Force Measurement Method, described herein.

Referring to FIG. 17, the bottom fixture 1100 is a pneumatic clamping system used to secure the specimen 1117 horizontally for testing. The fixture is built of a box 1103 made of 6.4 mm Plexiglass with a top 1101 and a bottom 1102 both made of 9.5 mm thick aluminum plates. The bottom 1102 plate is attached to the bottom mount of the tensile tester via an adapter 1104 and locking collar 1105 used to secure the fixture orthogonal to the mount of the tensile tester. Interior to the box a movable plate 1106 made of 9.5 mm thick aluminum is attached to two pneumatic cylinders 1107 and 1108 used to raise and lower the test specimen 1117. A rubber gasket 1113 is affixed on the bottom side of the top plate 1101 with a matching rubber gasket 1114 affixed to the top of the movable plate 1106. A circular 50.1 mm diameter, vertically oriented orifice 1115 passes through the longitudinal and lateral center of the top plate 1101 and gasket 1113. A corresponding circular 50.1 mm diameter orifice 1116 is vertically aligned with orifice 1115 and passes through the movable plate 1106 and gasket 1114. Pressurized air 1110 is provided to a switch 1109 which is fluidly connected via tubing 1111, 1112 to the cylinders 1107, 1108 and is used to raise and lower the movable plate 1106. The air pressure is sufficient to hold the sample securely without slippage for testing.

The upper fixture includes a cylindrical plunger 1003 terminating in a ball 1004 with a diameter of 25.4 mm. The plunger has an adapter 1001 compatible with the mount on the load cell capable of securing the plunger orthogonal to the top plate 1101 of the bottom fixture. When the fixtures are assembled with the tester, the ball 1004 is vertically centered over orifices 1115 and 1116, and the center of the ball travels along a vertical path coincident with the vertical axes of the orifices. The gage length is set at 10 mm between the bottom surface of the ball 1004 and the bottom surface of gasket 1113.

Program the instrument for compression mode. Lower the crosshead at a rate of 500 mm/min for the specified engagement distance and return the crosshead to its original position. Record data from the force and distance channels at a rate of 100 Hz during the downward stroke. Run a measurement cycle on each sample for three specified crosshead distances: 15 mm (i.e., 5 mm engagement) 20 mm, (i.e., 10 mm engagement) and 25 mm (i.e., 15 mm engagement).

Test sample products are conditioned in a laboratory controlled at 23° C.±2 C.° and 50%±2% relative humidity. Place the sample on a flat bench, top sheet facing upward. Identify the longitudinal axis of the sample. Measure down 45 mm from the top edge of the absorbent structure along the longitudinal axis and mark with a dot. This is the center of the measurement site. Remove release paper (or adhesive coversheet) (if present) from the sample. Center the marked dot within the opening in the lower plate. Prior to securing the sample between the gaskets 1113, 1114, it should be gently pulled taut with approximately equal tension applied along two perpendicular directions, only to an extent sufficient eliminate sagging over the opening 1116. After pulling the sample taut, activate the switch 1109 to admit air into the cylinders 1107, 1108 and thereby raise the movable plate 1106, to secure the sample between the gaskets 1113, 1114. Zero the force and crosshead channels and start the program. After the test, lower the movable plate and remove the sample prior to analyzing the next sample. Testing is performed on seven (7) replicate samples at each of the 3 crosshead distances.

Construct a graph of force (N) verses displacement (mm) for each test run. Read the peak force (N) at from the graph and record to the nearest 0.01 N. Calculate the Conformability Force as the greatest slope of the curve utilizing a line segment that is at least 20% of the maximum force and record to the nearest 0.1 N/m. Report Conformability Force as the average obtained from seven replicate specimens to the nearest 1 N/m, at a displacement of the sample to 5 mm from its starting position (i.e., after the ball first contacts the sample it moves downward to a maximum of 5 mm).

High Speed Tensile Test

The High Speed Tensile Test is used to measure the Tensile Strength of a material sample at a relatively high strain rate. The method uses a suitable tensile tester such as an MTS 810, available from MTS Systems Corp., Eden Prairie, Minnesota, or equivalent, equipped with a servo-hydraulic actuator capable of facilitating speeds exceeding 1 m/s after 5 mm of crosshead displacement, and at least approximately 1.5 m/s after 10 mm of crosshead displacement. The tensile tester is fitted with a 50-lb force transducer (part 9712 B50 from Kistler North America, Amherst, New York, or equivalent), and a signal conditioner with a dual mode amplifier (part 5010 from Kistler North America, or equivalent).

Figure 23:
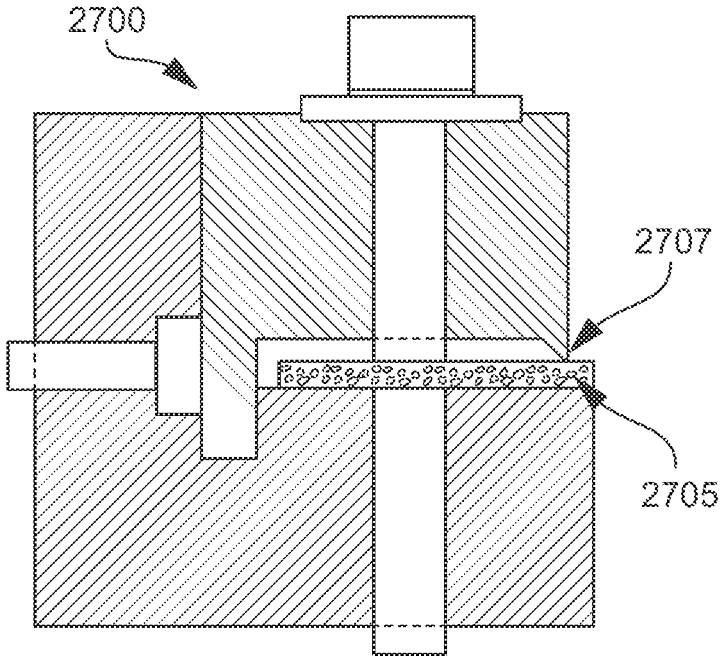
FIG. 23 is a cross-section view of a line contact grip used for the High Speed Tensile Test herein.
Figure 24:
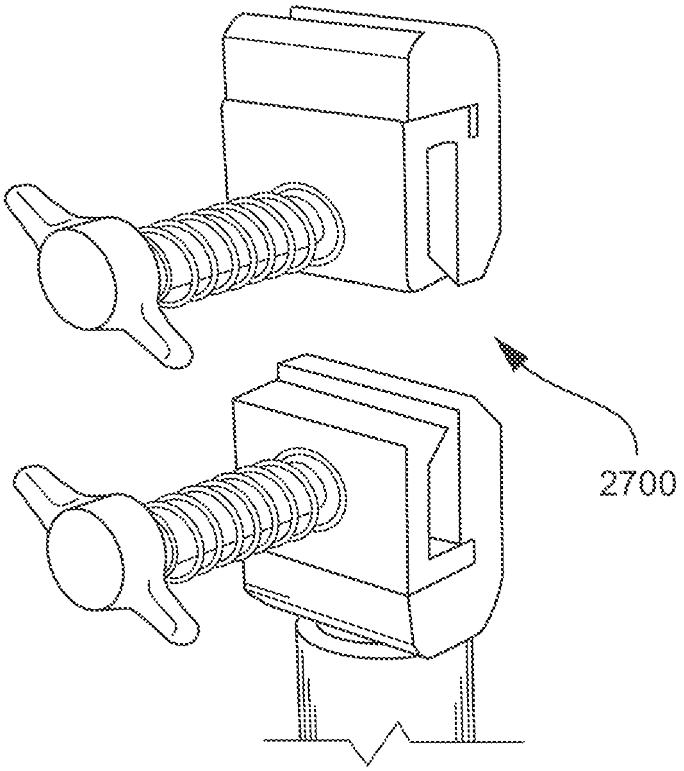
FIG. 24 is a perspective view of a pair of opposing line contact grips for use in the High Speed Tensile Test herein.

FIG. 23 is a cross-sectional view of a single line contact grip 2700 used in this test. The line grip 2700 is selected to provide a well-defined gauge and avoid undue slippage of the specimen. The specimen is positioned such that it has minimal slack. The apex 2707 of the grip 2700 is ground to give good gauge definition while avoiding damage or cutting of the specimen. A portion of the grip 2700 may be configured to include a material 2705 that reduces the tendency of a specimen to slip. FIG. 24 illustrates a pair of opposing line contact grips 2700 suitable for use in this test. A pair of grips of varying specific design but with equivalent function (i.e. capable of facilitating a well-defined 3-mm gauge length, no undue slippage, and at least as wide as the specimens analyzed) to those described above may be used alternatively.

For a nonwoven sample of interest, five like specimens having dimensions of 50.8 mm wide by 15 mm long are cut. The short dimension of each specimen is parallel to the machine direction of the nonwoven. If the specimens are extracted from finished absorbent article(s), the short dimension of the specimen is oriented parallel to the longitudinal axis of the absorbent article. The line contact grips are moved to a grip separation of 3.0 millimeters (i.e. the distance between the lines of contact between specimen and grip surface). The specimen is mounted in the line contact grips, and a thin piece of tape to help hold the specimen straight and flat while mounting in grips. (If used, tape must remain behind the lines of gripping so that it does not interfere with the specimen gauge during the test.) The line contact grips are moved closer together to put as much slack as possible into the film specimen without the line contact grips interfering with one another. Actuator movement is selected such that the specimen experiences relative grip speed of approximately 1 m/s at an engineering strain of 1 and 1.5 m/s at an engineering strain of 4. Typically, during testing, one of the line contact grips is kept stationary and the opposing line contact grip is moved, but forms where both line contact grips move are also contemplated herein.

The force and actuator displacement data generated during the test are recorded using a Nicolet Integra Model 10, 4-channel 1 Ms/s, 12-bit digitizer oscilloscope with the data acquisition frequency set at 50 kHz. The resulting data are expressed as force (measured in Newtons) versus engineering strain. The engineering strain (c) is dimensionless and is defined as $$\epsilon = \frac{L - L_0}{L_0} = \frac{z}{L_0}$$

where:

$L_0$ is the gauge length (i.e., the distance between lines of grip contact when the undeformed specimen is mounted in the grips). (The $L_0$ in the present example is 3.0 mm.)

L is grip position, the distance between lines of grip contact during the tensile test.

And z is displacement, defined as $z=L-L_0$.

Figure 25:
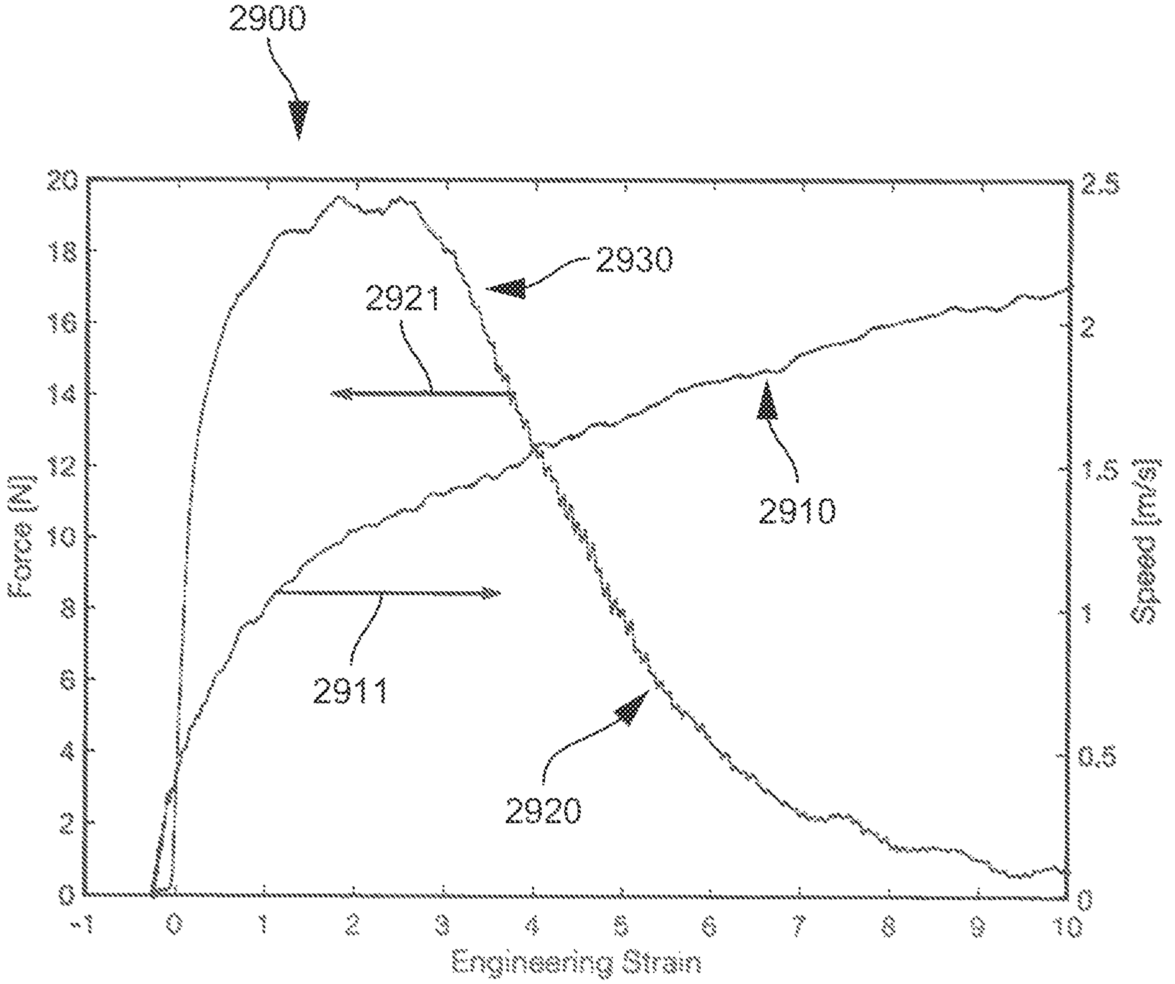
FIG. 25 is a graphical illustration of a suitable deformation regimen for the High Speed Tensile Test herein.

FIG. 25 illustrates a suitable example graph 2900 with two curves 2910 and 2920. The first curve 2910 illustrates a plot of actuator speed (i.e., the relative speed at which one grip is moving away from the other grip) versus engineering strain. The arrow 2911 points to the vertical axis at right used for the plot 2910. The second curve 2920 illustrates a plot of force versus engineering strain and uses the vertical axis at left, as indicated by the arrow 2921. The point of maximum force in the force versus engineering strain plot is identified. Moving toward higher engineering strain, the first point at which the force falls to equal to or less than 90% of the maximum force value is then identified, and the engineering strain at that point is defined as the Extensibility Parameter of the specimen and is recorded to the nearest 0.01. (The region in which this point is found is indicated by arrow 2930.)

The arithmetic mean of the five Extensibility Parameter values determined for each of the five like specimens is reported to the nearest 0.01 as the Extensibility Parameter of the material sample.

Enthalpies of Fusion and Crystallinity Test

The Enthalpies of Fusion and Crystallinity Test is used to determine the Enthalpy of Fusion and Percent Crystallinity parameters. The Enthalpies of Fusion and Crystallinity Test includes performing ASTM E793-06 with the following additional guidance. A specimen from a nonwoven web is die-cut from a sample nonwoven web. The mass of the specimen is 3±2 mg, and the mass of the specimen is recorded to the nearest 0.01 mg. (If multiple layers are required to achieve the requisite sample mass, the sample nonwoven web is folded such that multiple layers of the same nonwoven web are punched simultaneously to produce the specimen.) Dry nitrogen is used as the purge gas in a Differential Scanning Calorimeter (DSC). The range of testing temperature is from −90° C. to 200° C. The rate of increase temperature in DSC is 20° C./min, and the rate of decrease temperature is 20° C./min. The melting peak temperature is determined as described § 11 of ASTM E793-06. The mass-normalized enthalpy of fusion is calculated as specified in § 11 in ASTM E793-06 and reported as the Enthalpy of Fusion Parameter ($\Delta H_m$) in unit of Joules per gram (J/g) to the nearest 0.01 J/g.

From the Enthalpy of Fusion Parameter, the Percent Crystallinity is determined using the following equation $$\text{Percent Crystallinity}[\%] = \frac{\Delta H_m}{\Delta H_m^{\circ} \times W} \times 100\%$$

where $\Delta H_m$ is the mass-normalized Enthalpy of Fusion Parameter, $\Delta H_m^{\circ}$ is the mass-normalized Enthalpy of Fusion of 100% crystalline polypropylene (taken here to be 207 J/g), and W is the weight fraction of polypropylene.

Percent Crystallinity is reported to the nearest integer value in percentage.

In view of the foregoing description, the following non-limiting examples are contemplated herein:

A1. An absorbent article (10) comprising: a liquid permeable topsheet (20); a liquid impermeable backsheet (30); and an absorbent structure (40) disposed between the topsheet and backsheet, the absorbent article having a longitudinal axis (100) and a lateral axis (200);

wherein the absorbent article has been incrementally stretched along at least a first stretch direction (51*a*)

and a second stretch direction (51*b*) differing from the first stretch direction, such that:

the topsheet and the backsheet each have zones of permanent or plastic stretch deformation (20*s*, 30*s*) disposed substantially along two respective groups of lines of deformation (50), a first group of lines of deformation (50) being substantially perpendicular to the first stretch direction (51*a*) and a second group of lines of deformation (50) being substantially perpendicular to the second stretch direction (51*b*); and the topsheet and the backsheet each have zones (20*u*, 30*u*) that are relatively less deformed, or substantially undeformed, between the lines of deformation (50).

A2. The article of example A1, wherein the two groups of lines of deformation (50) form respective angles (α) and (β) with respect to the longitudinal axis (100), that are each 5 degrees to 85 degrees, more preferably 15 degrees to 70 degrees, and even more preferably 30 degrees to 60 degrees, and any subranges within these ranges.

A3. The article of examples A1 or A2, wherein the absorbent structure comprises a layer of absorbent foam material, preferably a HIPE foam material, and the layer of absorbent foam material is fractured substantially along the lines of deformation (50) into a plurality of discrete pieces (40*p*), wherein all or a subplurality of the discrete pieces (40*p*) are separated from neighboring pieces by gaps (40*s*).

A4. The article of example A3, wherein the discrete pieces (40*p*) have an average x-y planar size, across the entirety of the absorbent structure, no greater than 15 mm, more preferably no greater than 10 mm, still more preferably no greater than 7 mm, and even more preferably no greater than 5 mm.

A5. The article of any of examples A1 to A4, wherein the absorbent structure has an average caliper (C) and the gaps (40*s*) have an average x-y planar gap size (GS), across the entirety of the absorbent structure, of at least (0.04×C), more preferably (0.12×C), still more preferably (0.24×C), and even more preferably (0.4×C), or from (0.04×C) to (0.48×C), or any sub-range therewithin.

A6. The article of any of examples A1 to A5, wherein the backsheet (30) comprises a polymeric film.

A7. The article of any of examples A1 to A6, wherein the topsheet (20) comprises a nonwoven web material.

A8. The article of example A7, wherein the nonwoven web material is a spunbond nonwoven web material.

A9. The article of any of examples A1 to A8 wherein a deposit of an adhesive (45) is disposed between the absorbent structure (40) and the topsheet (20).

A10. The article of any of examples A1 to A9, wherein a deposit of an adhesive (45) is disposed between the absorbent structure (40) and the backsheet (30).

A11. The article of either of examples A9 or A10, wherein a deposit of adhesive between the absorbent structure and the topsheet is in the form of sprayed discrete droplets.

A12. The article of any of examples A9 to A11, wherein a deposit of adhesive between the absorbent structure and the backsheet is in the form of a continuous film of adhesive.

A13. The article of any of examples A9 to A12, wherein the adhesive functions to hold discrete pieces (40*s*) in position with respect to each other, within an x-y plane occupied by the absorbent structure.

A14. The article of any of examples A1 to A13, wherein substantially the entirety or the entirety of the article has been incrementally stretched along the first stretch direction (51*a*) and the second stretch direction (51*b*), in a pattern of stretched zones and unstretched zones substantially lacking any areas of discontinuity.

A15. The article of any of examples A1 to A14, configured as or incorporated into a feminine hygiene article.

A16. The article of any of examples A1 to A14, configured as or incorporated into a wearable incontinence article.

A17. The article of any of examples A1 to A14, incorporated into an adult underpants garment.

A18. The article of any of examples A1 to A14, incorporated into a diaper or child's training pants.

A19. A method for manufacturing an absorbent article (10), comprising the steps of:

providing a topsheet material comprising an extensible nonwoven web material;

providing a backsheet material comprising an extensible film;

providing an absorbent structure material;

combining the topsheet material, backsheet material and absorbent structure material to form a composite web (400) in which the absorbent structure material is disposed between the topsheet material and the backsheet material to form an absorbent structure (40);

conveying the composite web (400) through a first nip between a first pair of deforming rollers (302, 306, 307, 308) configured with respective mating/engaging ridges (302*d*, 306*d*, 307*d*, 308*d*) and grooves (302*e*, 306*e*, 307*e*, 308*e*), and thereby incrementally stretching the composite web along a first deformation direction (51*a*, 51*b*), whereby the topsheet material and backsheet material are each permanently/plastically deformed along parallel first lines of deformation (50) oriented substantially perpendicularly to the first deformation direction;

conveying the composite web (400) through a second nip between a second pair of deforming rollers configured with respective mating/engaging ridges (302*d*, 306*d*, 307*d*, 308*d*) and grooves (302*e*, 306*e*, 307*e*, 308*e*), and thereby incrementally stretching the composite web along a second deformation direction (51*a*, 51*b*) differing from the first deformation direction, whereby the topsheet material and backsheet material are each permanently/plastically deformed along parallel second lines of deformation (50) oriented substantially perpendicularly to the second deformation direction.

A20. The method of example A19, where the absorbent structure material fractures upon passage through the first nip and the second nip, thereby forming a plurality of discrete pieces (40*p*) of fractured absorbent structure material between the topsheet material and the backsheet material.

A21. The method of either of examples A19 or A20, further comprising the step of disposing an adhesive in a first location between a wearer-facing surface of the absorbent structure material and the topsheet material.

A22. The method of any of examples A19 to A21, further comprising the step of disposing an adhesive in a second location between an outward-facing surface of the absorbent structure material and the backsheet material.

A23. The method of either of examples A21 or A22, wherein the adhesive is disposed in the form of discrete droplets.

A24. The method of example A22, wherein the adhesive is disposed in the form of a continuous film.

A25. The method of any of examples A19 to A24, wherein the absorbent structure material is an absorbent foam material.

A26. The method of example A25, wherein the absorbent foam material is a HIPE foam material.

A27. The method of any of examples A19 to A25, wherein at least one and preferably both of the first and second pairs of deforming rollers comprises mating helical configurations of ridges (307*d*, 308*d*) and grooves (308*d*, 308*e*).

A28. The method of example A27, wherein the at least one and preferably both of the first and second pairs of deforming rollers is configured with a helix angle (γ1, γ2) selected to effect straining of the composite web along a strain direction (51*a*, 51*b*) that forms an angle (α, (β) with a lateral axis of the article, of 5 degrees to 85 degrees, more preferably 15 degrees to 70 degrees, and even more preferably 30 degrees to 60 degrees, and/or, effects lines of deformation (50) along the article that form an angle (α, β) with a longitudinal axis of the article, of 5 degrees to 85 degrees, more preferably 15 degrees to 70 degrees, and even more preferably 30 degrees to 60 degrees.

A29. The method of example A20 or any example depending therefrom, wherein the deforming rollers are configured to effect fracture the absorbent structure material into pieces (40*p*) having an average x-y planar size, across an entirety of an absorbent structure of the article, no greater than 15 mm, more preferably no greater than 10 mm, still more preferably no greater than 7 mm, and even more preferably no greater than 5 mm.

A30. The method of example A20 or any example depending therefrom wherein the deforming rollers are configured to effect fracture the absorbent material into pieces (40*p*) having gaps (40*s*) therebetween, having an average x-y planar gap size, across an entirety of an absorbent structure of the article, of at least (0.04×C), more preferably (0.16×C), still more preferably (0.28×C), and even more preferably (0.4×C), or from (0.04×C) to (0.48×C), or any sub-range therewithin, wherein "C" is the average caliper of the absorbent structure (40).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "approximately 40 mm."

Where ranges of measured quantities or property values are described and/or recited as characterizations of subject matter contemplated herein, such ranges are deemed to include and contemplate any and all sub-ranges within the ranges.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a longitudinal axis and a lateral axis;

a liquid permeable topsheet having a garment-facing surface and an opposing wearer-facing surface;

a liquid impermeable backsheet having a garment-facing surface and an opposing wearer-facing surface; and an absorbent structure comprising an open-celled absorbent foam material disposed between the topsheet and the backsheet, wherein the absorbent article has been incrementally stretched along at least a first stretch direction and a second stretch direction differing from the first stretch direction, such that:

the topsheet and the backsheet each comprise plastically stretched zones disposed substantially along a first plurality of lines of deformation being substantially perpendicular to the first stretch direction and a second plurality of lines of deformation being substantially perpendicular to the second stretch direction;

wherein the absorbent foam material is fractured substantially along the first plurality of lines of deformation and the second plurality of lines of deformation into a plurality of discrete foam pieces, wherein the plurality of discrete foam pieces are arranged in a pattern extending across the entire absorbent structure with no breaks or discontinuities in the pattern, and wherein the discrete foam pieces are separated from neighboring pieces by a gap of from about 0.3 mm to about 1.2 mm;

wherein from about 15 gsm to about 35 gsm of an adhesive is positioned between the garment-facing surface of the topsheet and a wearer-facing surface of the discrete foam pieces and bonds the discrete foam pieces to the topsheet;

wherein from about 15 gsm to about 35 gsm of an adhesive is positioned between the wearer-facing surface of the backsheet and a garment-facing surface of the discrete foam pieces and bonds the discrete foam pieces to the backsheet; and wherein the adhesive positioned between the topsheet and the discrete foam pieces and the adhesive positioned between the backsheet and the discrete foam pieces each comprise an elastic formulation utilizing a styrene/isoprene/styrene (SIS) building block.

2. The absorbent article of claim 1, wherein the adhesive is in the form of sprayed discrete droplets.

3. The absorbent article of claim 1, wherein the adhesive that bonds the discrete foam pieces to the backsheet is in the form of a continuous film of adhesive.

4. The absorbent article of claim 1, wherein the discrete foam pieces are arranged in a continuous pattern across the absorbent structure, wherein the discrete foam pieces have an average x-y planar size of from about 1.5 mm to about 15 mm.

5. The absorbent article of claim 1, wherein the absorbent structure has an average caliper (C), wherein the gap between the discrete foam pieces have an average x-y planar gap size of from 0.04×C to 0.48×C.

6. The absorbent article of claim 1, wherein the backsheet comprises a polymeric film having a basis weight of from about 20 gsm to about 28 gsm.

7. The absorbent article of claim 1, wherein the topsheet is a spunbond nonwoven material.

8. The absorbent article of claim 1, wherein the first plurality of lines of deformation form an angle α with respect to the longitudinal axis and the second plurality of lines of deformation form an angle β with respect to the longitudinal axis, wherein the angle α and the angle β are each from about 5 degrees to about 85 degrees.

9. The absorbent article of claim 1, wherein the absorbent article has a Conformability Force of from about 140 N/m to about 1500 N/m.

10. The absorbent article of claim 1, wherein substantially the entirety or the entirety of the absorbent article has been incrementally stretched along the first stretch direction and the second stretch direction, in a pattern of plastically stretched zones and unstretched zones substantially lacking any areas of discontinuity.

11. An absorbent article comprising:

a longitudinal axis and a lateral axis;

a liquid permeable topsheet having a garment-facing surface and an opposing wearer-facing surface;

a liquid impermeable backsheet having a garment-facing surface and an opposing wearer-facing surface; and an absorbent structure comprising an open-celled absorbent foam material disposed between the topsheet and the backsheet;

wherein the topsheet and the backsheet each comprise plastically stretched zones disposed substantially along a first plurality of lines of deformation extending in a first direction and a second plurality of lines of deformation extending in a second direction;

wherein the first plurality of lines of deformation form an angle α with respect to the longitudinal axis and the second plurality of lines of deformation form an angle β with respect to the longitudinal axis, wherein the angle α and the angle β are each from about 5 degrees to about 85 degrees;

wherein the absorbent structure comprises a plurality of discrete foam pieces arranged along the lines of deformation, wherein the discrete foam pieces are separated from neighboring pieces by a gap of from about 0.3 mm to about 1.2 mm, thereby avoiding mechanical edge-to-edge interference between adjacent discrete foam pieces when the absorbent article is bent in a z-direction;

wherein from about 15 gsm to about 35 gsm of an adhesive is positioned between a garment-facing surface of the topsheet and a wearer facing surface of the discrete foam pieces and bonds the discrete foam pieces to the topsheet;

wherein the discrete foam pieces have an average x-y planar size of from about 1.5 mm to about 15 mm.

12. The absorbent article of claim 11, wherein the discrete foam pieces comprise a high internal phase emulsion foam.

13. The absorbent article of claim 11, wherein a portion of the adhesive penetrates into the garment-facing surface of the topsheet and the wearer-facing surface of the discrete foam piece.

14. An absorbent article comprising:

a longitudinal axis and a lateral axis;

a liquid permeable topsheet;

a liquid impermeable backsheet having a basis weight of from about 20 gsm to about 28 gsm; and an absorbent structure comprising a high internal phase emulsion foam disposed between the topsheet and the backsheet;

wherein the topsheet and the backsheet each comprise plastically stretched zones, wherein a portion of the plastically stretched zones extend continuously and without breaks from a first side of the topsheet to a second side of the topsheet;

wherein the absorbent structure comprises a plurality of discrete foam pieces arranged in a pattern extending across the entire absorbent structure, wherein the discrete foam pieces are separated from neighboring pieces by a gap of from about 0.3 mm to about 1.2 mm;

wherein the plastically stretched zones are disposed substantially along a first plurality of lines of deformation and a second plurality of lines of deformation, wherein the first plurality of lines of deformation form an angle α with respect to the longitudinal axis and the second plurality of lines of deformation form an angle β with respect to the longitudinal axis, wherein the angle α and the angle β are each from about 30 degrees to about 60 degrees; and wherein from about 15 gsm to about 35 gsm of an adhesive is positioned between a garment-facing surface of the topsheet and a wearer-facing surface of the discrete foam pieces and bonds the discrete foam pieces to the topsheet.

15. The absorbent article of claim 14, wherein the first side of the topsheet is a first longitudinal side and extends in a direction substantially parallel to the longitudinal axis.

16. The absorbent article of claim 15, wherein the second side of the topsheet is a second longitudinal side and extends in a direction substantially parallel to the longitudinal axis.

* * * * *